US011744748B2

(12) United States Patent
Chmielewski et al.

(10) Patent No.: US 11,744,748 B2
(45) Date of Patent: Sep. 5, 2023

(54) DRYNESS LAYER LAMINATE FOR ABSORBENT ARTICLES

(71) Applicant: ATTENDS HEALTHCARE PRODUCTS, INC., Raleigh, NC (US)

(72) Inventors: Harry Chmielewski, Wake Forest, NC (US); Michael Kalmon, Fredericktown, OH (US); Matthew Ashcraft, Raleigh, NC (US); Paul Ducker, St. Simons Island, GA (US)

(73) Assignee: ATTENDS HEALTHCARE PRODUCTS, INC., Greenville, NC (US)

( * ) Notice: Subject to any disclaimer, the term of this patent is extended or adjusted under 35 U.S.C. 154(b) by 943 days.

(21) Appl. No.: 16/424,192

(22) Filed: May 28, 2019

(65) Prior Publication Data
US 2019/0358097 A1    Nov. 28, 2019

Related U.S. Application Data

(60) Provisional application No. 62/677,168, filed on May 28, 2018.

(51) Int. Cl.
*A61F 13/537*    (2006.01)
*A61F 13/534*    (2006.01)
*A61F 13/494*    (2006.01)
*A61F 13/53*    (2006.01)
*A61F 13/15*    (2006.01)

(52) U.S. Cl.
CPC .... *A61F 13/53747* (2013.01); *A61F 13/4946* (2013.01); *A61F 13/5376* (2013.01); *A61F 13/53418* (2013.01); *A61F 2013/15861* (2013.01); *A61F 2013/53445* (2013.01); *A61F 2013/53454* (2013.01); *A61F 2013/530985* (2013.01)

(58) Field of Classification Search
CPC ............ A61F 13/53747; A61F 13/4946; A61F 13/53418; A61F 13/5376; A61F 2013/15861; A61F 2013/530985; A61F 2013/53445; A61F 2013/53454
See application file for complete search history.

(56) References Cited

U.S. PATENT DOCUMENTS

| | | |
|---|---|---|
| 3,563,243 A | 2/1971 | Lindquist |
| 4,100,324 A | 7/1978 | Anderson et al. |
| 4,114,621 A | 9/1978 | Mims, Jr. |
| 4,443,512 A | 4/1984 | Delvaux |
| 4,573,986 A | 3/1986 | Minetola et al. |
| 4,670,011 A | 6/1987 | Mesek |
| 4,743,246 A | 5/1988 | Lawson |
| 4,808,177 A | 2/1989 | Desmarais et al. |
| 4,940,464 A | 7/1990 | Van Gompel et al. |
| 5,021,051 A | 6/1991 | Takashi |
| 5,458,592 A | 10/1995 | Abuto et al. |
| 5,462,538 A | 10/1995 | Korpman |
| 5,486,167 A | 1/1996 | Dragoo et al. |
| 5,494,622 A | 2/1996 | Heath et al. |
| 5,520,673 A | 5/1996 | Yarbrough et al. |
| 5,552,012 A | 9/1996 | Morris et al. |
| 5,558,655 A | 9/1996 | Jezzi et al. |
| 5,562,645 A | 10/1996 | Tanzer et al. |
| 5,593,399 A | 1/1997 | Tanzer et al. |
| 5,624,426 A | 4/1997 | Roe et al. |
| 5,643,243 A | 7/1997 | Klemp |
| 5,646,180 A | 7/1997 | Chaturvedi |
| 5,735,838 A | 4/1998 | Roennberg et al. |
| 5,785,696 A | 7/1998 | Inoue et al. |
| 5,904,675 A | 5/1999 | Robinson et al. |
| 5,944,706 A | 8/1999 | Palumbo et al. |
| 6,037,518 A | 3/2000 | Guidotti et al. |
| 6,159,190 A | 12/2000 | Mitsugu et al. |
| 6,174,302 B1 | 1/2001 | Yoshinori |
| 6,191,340 B1 | 2/2001 | Carlucci et al. |
| 6,316,687 B1 | 11/2001 | Davis et al. |
| 6,372,953 B1 | 4/2002 | Young et al. |
| 6,380,456 B1 | 4/2002 | Goldman |
| 6,436,234 B1 | 8/2002 | Chen et al. |
| 6,455,114 B1 | 9/2002 | Goldhirsch et al. |
| 6,479,415 B1 | 11/2002 | Erspamer et al. |

(Continued)

FOREIGN PATENT DOCUMENTS

| | | |
|---|---|---|
| CN | 1230396 | 10/1999 |
| CN | 102781383 | 11/2012 |

(Continued)

OTHER PUBLICATIONS

International Preliminary Report for corresponding Application No. PCT/US2014/028292, dated Sep. 15, 2015.
International Preliminary Report for corresponding Application No. PCT/US2014/028414, dated Sep. 15, 2015.
International Search Report and Written Opinion for corresponding Application No. PCT/US2014/028292, dated Aug. 11, 2014.
International Search Report and Written Opinion for corresponding Application No. PCT/US2014/028414, dated Mar. 14, 2014.
International Search Report and Written opinion issued in International Application No. PCT/US2019/034201, dated Sep. 9, 2019.
Office Action issued in Chinese Patent Application No. 201480021203. 7, dated Mar. 2, 2018.
Office Action issued in Japanese Patent Application No. 2016-502781, dated Mar. 26, 2018.

(Continued)

*Primary Examiner* — Alma Pipic
(74) *Attorney, Agent, or Firm* — Norton Rose Fulbright US LLP

(57) ABSTRACT

The present disclosure relates to absorbent garments having a dryness layer that can comprise one or more laminates and one or more channels to facilitate liquid acquisition and retention. Laminate(s) can include an absorbent lamina disposed between substrate laminae, each comprising tissue and/or a nonwoven. Some dryness layers can have a folded laminate that defines a longitudinally-extending channel. Some dryness layers can have two or more laminate strips that are laterally spaced apart along a width of the dryness layer such that one or more longitudinally-extending channels are defined therebetween.

15 Claims, 11 Drawing Sheets

(56) References Cited

U.S. PATENT DOCUMENTS

| | | |
|---|---|---|
| 6,610,903 B1 | 8/2003 | Latimer et al. |
| 6,646,180 B1 | 11/2003 | Chmielewski |
| 6,667,424 B1 | 12/2003 | Hamilton et al. |
| 6,675,702 B1 | 1/2004 | Maksimow |
| 6,746,976 B1 | 6/2004 | Urankar et al. |
| 6,764,478 B2 | 7/2004 | Langdon et al. |
| 6,923,926 B2 | 8/2005 | Walter et al. |
| 6,976,978 B2 | 12/2005 | Ruman et al. |
| 7,175,613 B2 | 2/2007 | Sugiyama et al. |
| 7,232,300 B2 | 6/2007 | Walter |
| 7,910,797 B2 | 3/2011 | Nandrea et al. |
| 8,039,684 B2 | 10/2011 | Guidotti et al. |
| 9,238,089 B2 | 1/2016 | Chmielewski et al. |
| 9,398,986 B2 | 7/2016 | Pasqualoni et al. |
| 10,092,674 B2 | 10/2018 | Chmielewski et al. |
| 10,166,156 B2 | 1/2019 | Yeoh |
| 2001/0031956 A1 | 10/2001 | Drevik |
| 2002/0072725 A1 | 6/2002 | Kolby-Falk |
| 2002/0115969 A1 | 8/2002 | Maeda et al. |
| 2002/0128625 A1 | 9/2002 | Masahito et al. |
| 2003/0018311 A1 | 1/2003 | Graef et al. |
| 2003/0135178 A1 | 7/2003 | Hansen |
| 2003/0225384 A1 | 12/2003 | Zenker et al. |
| 2004/0015142 A1 | 1/2004 | Johnston et al. |
| 2004/0054343 A1 | 3/2004 | Barnett et al. |
| 2004/0102747 A1 | 5/2004 | Bell et al. |
| 2004/0236294 A1 | 11/2004 | Drzewiecki et al. |
| 2005/0113790 A1 | 5/2005 | Minako et al. |
| 2005/0118916 A1 | 6/2005 | Ducker et al. |
| 2007/0197897 A1 | 8/2007 | Tsang et al. |
| 2010/0137773 A1 | 6/2010 | Gross et al. |
| 2010/0256584 A1 | 10/2010 | Litvay |
| 2010/0318047 A1 | 12/2010 | Ducker et al. |
| 2011/0162989 A1 | 7/2011 | Ducker et al. |
| 2011/0208145 A1 | 8/2011 | Zhang et al. |
| 2011/0319855 A1 | 12/2011 | Lash |
| 2012/0004632 A1 | 1/2012 | Zhang et al. |
| 2012/0035575 A1 | 2/2012 | Ehrnsperger et al. |
| 2012/0053545 A1 | 3/2012 | Love et al. |
| 2012/0144790 A1 | 6/2012 | Cambo et al. |
| 2012/0148821 A1 | 6/2012 | Ducker et al. |
| 2012/0238984 A1 | 9/2012 | Paldey |
| 2013/0046263 A1 | 2/2013 | Fukudome et al. |
| 2014/0276510 A1 | 9/2014 | Ducker et al. |
| 2014/0315034 A1 | 10/2014 | Akiyama et al. |
| 2015/0173959 A1 | 6/2015 | Carlucci et al. |
| 2015/0245958 A1 | 9/2015 | Chmielewski et al. |
| 2015/0257946 A1 | 9/2015 | Macura et al. |
| 2016/0220427 A1 | 8/2016 | Ducker |
| 2016/0272979 A1 | 9/2016 | Roe et al. |
| 2017/0014279 A1 | 1/2017 | Bianchi et al. |
| 2017/0065466 A1 | 3/2017 | Szypka |
| 2017/0079858 A1 | 3/2017 | Willhaus et al. |
| 2017/0258651 A1 | 9/2017 | Hammons et al. |
| 2017/0360628 A1 | 12/2017 | Chmielewski et al. |
| 2018/0214319 A1 | 8/2018 | Inoue et al. |
| 2018/0243145 A1 | 8/2018 | Wright et al. |
| 2018/0338870 A1 | 11/2018 | Kreuzer |
| 2019/0328587 A1 | 10/2019 | Saevecke et al. |

FOREIGN PATENT DOCUMENTS

| | | |
|---|---|---|
| CN | 102970953 | 3/2013 |
| CN | 103006385 | 4/2013 |
| CN | 104780881 | 7/2015 |
| EP | 0438113 | 7/1991 |
| EP | 0556996 | 8/1993 |
| EP | 1027874 | 8/2000 |
| EP | 1447065 | 7/2002 |
| EP | 1245209 | 10/2002 |
| EP | 3053556 | 2/2003 |
| EP | 1609448 | 12/2005 |
| EP | 3287108 | 2/2018 |
| JP | 2002085450 | 3/2002 |
| JP | 2003026701 | 1/2003 |
| JP | 2005537852 | 12/2005 |
| JP | 2012010972 | 1/2012 |
| RU | 64902 | 7/2007 |
| RU | 112038 | 1/2012 |
| WO | WO 1995/013776 | 5/1995 |
| WO | WO 9605790 | 2/1996 |
| WO | WO 1999/049826 | 10/1999 |
| WO | WO 2000/030585 | 6/2000 |
| WO | WO 2000/038749 | 7/2000 |
| WO | WO 2000/075427 | 12/2000 |
| WO | WO 2001/005440 | 1/2001 |
| WO | WO 01/89439 | 11/2001 |
| WO | WO 2004/012639 | 2/2004 |
| WO | WO 2014/083501 | 6/2014 |
| WO | WO 2014144131 | 9/2014 |
| WO | WO 2015/129367 | 9/2015 |
| WO | WO 2015/171972 | 11/2015 |
| WO | WO 2018/112229 | 6/2018 |

OTHER PUBLICATIONS

Office Action issued in Corresponding Japanese Application No. 2019-531657, dated Oct. 4, 2021 (English Translation provided).
Chmielewski, Harry J.; International Preliminary Report on Patentability for PCT Application No. PCT/US2014/028414, filed Sep. 15, 2015, 9 pgs.
Chmielewski, Harry J; International Search Report and Written Opinion for PCT Application No. PCT/US2014/028414, filed Mar. 14, 2014, 10 pgs.
Ducker, Paul M ; Issue Notification for U.S. Appl. No. 14/212,754, filed Mar. 14, 2014, dated Dec. 29, 2015, 1 pg.
Ducker, Paul M., International Preliminary Report for PCT Application No. PCT/US2014/028292, filed Mar. 14, 2014, dated Sep. 15, 2015, 6 pgs.
Ducker, Paul M., International Search Report and Written Opinion for PCT Application No. PCT/US2014/028292, filed Mar. 14, 2014, dated Aug. 11, 2014, 7 pgs.
Ducker, Paul M.; Corrected Notice of Allowability for U.S. Appl. No. 14/212,754, filed Mar. 14, 2014, dated Sep. 25, 2015, 8 pgs.
Ducker, Paul M.; Non-Final Office Action for U.S. Appl. No. 14/212,754, filed Mar. 14, 2014, dated Jan. 14, 2015, 21 pgs.
Ducker, Paul M.; Notice of Allowance for U.S. Appl. No. 14/212,754, filed Mar. 14, 2014, dated Aug. 17, 2015, 9 pgs.
Ducker, Paul M.; U.S. Patent Application entitled: Absorbent Structure With Discrete Acquisition Cells, having U.S. Appl. No. 14/212,754, filed Mar. 14, 2014, 30 pgs.
Ducker, Paul; U.S. Provisional Application entitled: Absorbent Structures, having U.S. Appl. No. 61/789,444, filed Mar. 15, 2013.
Extended European Search Report Issued in Corresponding European Patent Application No. 18813262.5, dated Feb. 16, 2021.
Extended European Search Report Issued in Corresponding European Application No. 16747100.2, dated Jun. 4, 2018.
International Search Report and Written Opinion Issued in Corresponding International Application No. PCT/US2020/015397, dated Jul. 1, 2020.
International Search Report and Written Opinion issued in International Patent Application No. PCT/US2016/16142, dated Apr. 8, 2016.
Office Action Issued in Chinese Application No. 201680011883.3, dated Mar. 3, 2020.
International Search Report and Written Opinion for Application No. PCT/US2020/046065, dated Oct. 23, 2020, 16 pages.
International Search Report and Written Opinion Issued in Corresponding PCT Patent Application No. PCT/US2019/064126, dated Feb. 20, 2020.
International Search Report and Written Opinion Issued in PCT Patent Application No. PCT/US2019/064136, dated Feb. 21, 2020.
Decision to Grant and Search Report issued in related Russian Application No. 2020142738, dated Dec. 1, 2022 (English translation).

DRYNESS LAYER LAMINATE FOR ABSORBENT ARTICLES

CROSS-REFERENCED TO RELATED APPLICATIONS

This application claims priority to and the benefit of U.S. Provisional Patent Application No. 62/677,168 filed May 28, 2018, which application is incorporated by reference in its entirety.

FIELD OF INVENTION

The present invention relates generally to absorbent garments and, more particularly, to absorbent garments having a dryness layer to facilitate liquid acquisition and retention.

BACKGROUND

Absorbent products, such as baby diapers, training pants, and adult incontinence briefs and underwear, all of which may be made in disposable forms. "Disposable" refers to articles that are designed to be discarded after a limited use rather than being laundered or otherwise restored for reuse. Disposable absorbent products have met with widespread acceptance in the marketplace for a variety of applications, including infant and adult incontinence care, in view of the manner in which such products can provide effective and convenient liquid absorption and retention while maintaining the comfort of the wearer. Such disposable absorbent articles often include a topsheet that is configured to be closest to the wearer during use, a liquid-impermeable backsheet or outer cover, and an absorbent core between the topsheet and the backsheet. In some instances, such disposable absorbent articles also include an acquisition-distribution layer (ADL) disposed between the topsheet and the absorbent core. Elasticated standing leg cuffs and leg gathers are also often used in such articles to provide improved fit and reduced leakage around a wearer's legs, relative to articles without such cuffs or gathers.

U.S. Pat. No. 4,670,011 discloses certain prior art examples of diapers, and U.S. Pat. Nos. 6,976,978 and 4,940,464 disclose certain prior art examples of disposable incontinence garments or training pants.

One example of such a disposable absorbent article is shown in FIGS. 1A-1B, which depict a lower plan view and a perspective view, respectively, of adult protective underwear 10. Underwear 10 includes a chassis 14 having a front waist portion 18, an opposing rear waist portion 22, and a crotch portion 26 extending longitudinally between front and rear waist portions 18, 22. Chassis 14 further includes a backsheet 30 defining an outer surface and configured to face away from a wearer during use of the diaper, and topsheet 34 defining an opposing body facing surface and configured to face a wearer during use of the diaper.

As shown in FIGS. 1A-1B, underwear 10 further includes a pair of front elastic side panels 38 and a pair of rear elastic side panels 42 configured to couple rear waist portion 22 to front waist portion 18 in a well-known configuration in which a left side 46 of the chassis defines a first leg opening 50 for a wearer's left leg, and in which a right side 54 of the chassis defines a second leg opening 58 for the wearer's right leg. In the depicted configuration, each of side panels 38, 42 includes a connection portion 62 configured to be coupled to a connection portion 62 of another of side panels 38, 42. Specifically, connection portion 62 of the left one of front side panels 38 is configure to be coupled to connection portion 62 of the left one of rear side panels 42, and connection portion 62 of the right one of front side panels 38 is configure to be coupled to connection portion 62 of the right one of rear side panels 42, such that the waist portions 18, 22 and side panels, 38, 42 cooperate to define a waist opening 66 as shown in FIG. 1B. Connection portions 62 of the respective side panels can be permanently coupled together to define a tear-able side seam 70, such as, for example, via adhesive, ultrasonic, or thermal bonds. Such tear-able side seams generally cannot be refastened, and thereby render an article unusable once opened. Alternatively, connection portions 62 of the respective side panels can be removably coupled to define a refastenable or adjustable side seam, such as, for example, via hook-and-loop fasteners. Hook and loop fasteners are mechanical fasteners that include hooks, such as in a hook fastener portion, that are configured to engage loops in a loop fastener portion or in fibers of a sheet of fabric; for example, a nonwoven or woven fabric with fibers that define open or loop-like regions into which the hooks can extend and engage. Examples of such hook and loop fasteners may be referred to as VELCRO.

As is known in the art, underwear 10 can include one or more elastic elements coupled to the chassis such that the one or more elastic elements resist expansion of a circumference of the first leg opening and resist expansion of a circumference of the second leg opening. For example, as shown in FIG. 1A, the depicted embodiment of the chassis (14) includes a first elastic region 74 along right side 46, and a second elastic region 78 along left side 54. In some configurations, elastic regions 74, 78 can each be defined by one or more elastic strands, which may be referred to in the art as "leg elastics," coupled to the chassis, for example laminated between the topsheet or an additional leg cuff layer and the backsheet. In other configurations, elastic regions 74, 78 can each be defined by an elastic film coupled to the chassis, for example laminated between the topsheet and the backsheet. In configurations in which elastic regions 74, 78 are defined by elastic film, the regions can be defined by separate pieces of elastic film or by separate regions of a single piece of elastic film. As shown in FIG. 1A, elastic regions 74, 78 may be parallel to and/or extend along a majority of a length of each of sides 46 and 54, provided that the elastic regions are configured to provide a biasing force that resists expansion of the leg openings when the chassis is in its closed configuration and tends to contract the leg opening around a wearer's leg, as shown in FIG. 1B. Contraction of the leg opening to conform to the wearer's leg is desired for good containment of urine and feces in an absorbent product.

Another example of such a disposable absorbent article is shown in FIGS. 2A and 2B, which depict lower plan views of an adult incontinence brief 100. Brief 100 includes a chassis 104 having a front waist portion 108, an opposing rear waist portion 112, and a crotch portion 116 extending longitudinally between front and rear waist portions 108, 112. Chassis 104 further includes an outer surface 128 configured to face away from a wearer during use of the diaper, and an opposing body facing surface 132 configured to face a wearer during use of the diaper. In the view of FIG. 2A, a dashed leader extends from the body facing surface to reference numeral 132 because body facing surface 132 is opposite outer surface 128 and therefore not visible in the view of FIG. 2A.

As shown in FIG. 2A, brief 100 further includes a pair of closure members 136 configured to couple rear waist portion 112 to front waist portion 108 in a well-known configuration in which a left side 140 of the chassis defines a first leg opening for a wearer's left leg, and in which a right side 144 of the chassis defines a second leg opening for the wearer's right leg, similar in some respects to what is shown in FIG. 1B for training pant 10. In the depicted configuration, the closure members include a pair of back ears or back ear panels 148 each having a first end 152 bonded to rear waist portion 112 of chassis 104, and a second end 156 shown extending away from rear waist portion 112. "Bonded" refers to the joining, adhering, connecting, attaching, or the like, of two elements via adhesive(s), ultrasonic bond(s), and/or thermal bond(s). Two elements will be considered to be bonded together when they are bonded directly to one another or indirectly to one another, such as when each is directly bonded to intermediate elements.

Each closure member 136 further includes a fastener tab 160 with a first end 164 bonded to back ear 148, a second end 168 shown extending laterally outward from back ear 148, and a fastener portion 172 coupled to the fastener tab. Back ears 148 are each formed of a stretchable elastic material, such as a nonwoven laminate, that permits adjustments in the width and tension of back ears 148 to vary the form and fit of brief 100 when worn by a user.

Fastener tabs 160 are formed of an inelastic nonwoven material and carry fastener portions 172. Fastener portions 172 include strips of hook material configured to interact with a corresponding loop material in the well-known hook-and-loop fastener arrangement. Connection of closure members 136 to front waist portion 108 is facilitated by a landing zone 176 configured to be engaged by fastener portions 172. In this embodiment, landing zone 176 is defined by an anchoring member that includes a strip of loop material bonded to front waist portion 108 of chassis 104, for example, to the backsheet, and configured to be engaged by the hook material of fastener portions 172.

As shown in FIG. 2A, brief 100 also includes a pair of front ears 180 extending from opposite sides 140, 144 of chassis 104 with each of front ears 180 each having a first end 184 bonded to front waist portion 108 of chassis 104, and a second end 188 shown extending away from a respective side of front waist portion 108. Front ears 180 are each formed of a relatively soft nonwoven material and are each configured to be overlapped by the corresponding fastener tab 160 and/or back ear 148 to prevent the edges of fastener tab 160 from pinching, rubbing, or otherwise irritating a user's skin in use when fastening portions 172 are engaged with landing zone 176 to couple rear waist portion 112 to front waist portion 108. In some embodiments, front ears 180 include loop fastener portions or a fabric that is configured to be engaged by hook fastener portions such that fastener portions 172a can engage front ears 180.

Outer surface 128 is defined by a liquid-impermeable backsheet or cover 192 that defines outer surface 128, and a liquid-permeable topsheet 196 that defines body facing surface 132 and is configured to be closest to the wearer during use. "Liquid impermeable," when used in describing a layer or multi-layer laminate, means that a liquid, such as urine, will not pass through the layer or laminate, under ordinary use conditions, in a direction generally perpendicular to the plane of the layer or laminate at the point of liquid contact. "Lamination" is the technique of manufacturing a material in multiple layers, so that the composite material has benefits of all the combined layers, such as, for example, improved mechanical strength or durability, improved stability, lower permeability to water, and/or other properties.

A laminate includes two or more layers of material(s) that are permanently assembled by heat, pressure, ultrasonic welding, or adhesives.

As shown in FIG. 2B, the depicted embodiment include an absorbent core 200 disposed between topsheet 196 and backsheet 192. An "absorbent core" is a structure typically disposed between a topsheet and backsheet of an absorbent article and containing materials like SAP and/or cellulosic fibers that are configured to absorb liquid in the absorbent article.

As shown in FIG. 2B, brief 100 also includes an acquisition-distribution layer (ADL) 204 disposed between the topsheet and the absorbent core. "Layer" when used in the singular can be a single element or a plurality of elements. For example, a plurality of sheets may together define a single layer, such as, for example, a layer with a particular function to which the sheets of the layer contribute.

As is known in the art, brief 100 can include one or more elastic elements coupled to the chassis such that the one or more elastic elements resist expansion of a circumference of the first leg opening and resist expansion of a circumference of the second leg opening. For example, as shown in FIG. 2B, the depicted configuration of the chassis (104) includes a first elastic region 208 along first side 140, and a second elastic region 208 along second side 140. In some configurations, elastic regions 208 can each be defined by one or more elastic strands, which may be referred to in the art as "leg elastics," coupled to the chassis, for example laminated between the topsheet (or an additional leg cuff layer) and the backsheet. In other configurations, elastic regions 208 can each be defined by an elastic film coupled to the chassis, for example laminated between the topsheet (or an additional leg cuff layer) and the backsheet. In configurations in which elastic regions 208 are defined by elastic film, the regions can be defined by separate pieces of elastic film or by separate regions of a single piece of elastic film. As shown in FIG. 2B, elastic regions 208 may be parallel to and/or extend along a majority of a length of each of sides 140 and 144, provided that the elastic regions are configured to provide a biasing force that resists expansion of the leg openings when the chassis is in its closed configuration.

As shown in FIG. 2A, chassis 104 has an overall relaxed length 212.

Brief 100 of FIGS. 2A and 2B is typically packaged and sold in a folded, and unfastened configuration in which chassis 104 is folded in half such that rear waist portion 108 overlaps front waist portion 104, but fastener portions 172 do not engage landing zone 176. While brief 100 is described as an adult incontinence brief, brief 100 can also comprise a baby diaper or training pant.

Prior designs (e.g., underwear 10 and brief 100) that use a conventional absorbent core, such as a core comprising fluff and SAP, can exhibit long acquisition times. Poor liquid acquisition can cause leakage. Conventional ADLs designed to improve liquid acquisition times can cause free liquid to spread over the surface of the ADL, which also promotes leakage from the side and/or front of the core. Furthermore, absorbed liquid can migrate from the core to the wearer-facing surface of the garment, causing discomfort for the wearer. Accordingly, there is a need in the art for absorbent garments that can better acquire and retain liquid to promote comfort for the wearer.

SUMMARY

The present absorbent garments provide improved liquid acquisition and retention with a dryness layer. The present dryness layers can include laminate(s) having absorbent lamina(e) that comprise superabsorbent polymer and substrate lamina(e) that comprise a nonwoven and/or tissue. Such laminates can facilitate liquid acquisition and retention within the absorbent lamina(e) and/or an absorbent core. The present dryness layers can have one or more channels configured to receive liquid to promote the distribution and retention thereof. Channel(s) can be defined between folded layers of a laminate and/or between separate strips of laminate.

Some of the present absorbent garments comprise a chassis having opposing front and rear waist portions and a crotch portion extending longitudinally between the front and rear waist portions. Some garments have an absorbent core coupled to the crotch portion, which optionally comprises fluff and superabsorbent polymer (SAP). Some garments have a dryness layer extending longitudinally along the absorbent core. The chassis of some of the present garments comprises a backsheet and/or a topsheet, wherein, optionally, the absorbent core and the dryness layer are disposed between the backsheet and the topsheet.

In some garments, the absorbent core and the dryness layer each have a lateral width and a longitudinal length, wherein the width of the absorbent core at least 10% larger than the width of the dryness layer and/or the length of the absorbent core is at least 10% larger than the length of the dryness layer. The lateral width of some of the present dryness layers is between 65 and 85 millimeters (mm), and the longitudinal length of some of the present dryness layers is between 185 and 270 mm.

Some of the present dryness layers comprise a laminate that includes an absorbent lamina disposed between first and second substrate laminae. In some garments, the absorbent lamina comprises SAP. The SAP of the absorbent lamina, in some garments, has a basis weight between 60 and 120 grams per square meter (gsm). In some garments, the SAP of the absorbent lamina comprises particles, and ones of the particles having a diameter that is greater than or equal to 500 micrometers (μm) account for less than 10% of the mass of the particles. In some garments, the first substrate lamina comprises tissue and, in some of those garments, the tissue can be creped. The tissue of the first substrate lamina, in some garments, can have a basis weight between 14 and 20 gsm. In some garments, the second substrate lamina comprises a nonwoven which, for some of those garments, comprises a resin-bonded polymer fiber nonwoven. In some garments, the nonwoven of the second substrate lamina has a bass weight between 40 and 50 gsm.

In some garments, the laminate is longitudinally folded such that the dryness layer includes a base layer of the laminate and, within each of first and second longitudinally-extending edge regions, a folded layer of the laminate disposed on the base layer. The base layer, in some garments, spans a lateral width of the dryness layer. In some garments, each of the edge regions spans less than 50% of the width such that a longitudinally-extending channel is defined between the folded layers. In some garments, the channel has a lateral width between 8 and 20 mm, optionally between 8 and 12 mm. In some garments, the laminate is coupled to the absorbent core such that, for the base layer, the first substrate lamina is disposed closer to the absorbent core than is the second substrate lamina and, optionally, for each of the folded layers, the first substrate lamina is disposed further from the absorbent core than is the second substrate lamina. In some garments, for each of the folded layers the first substrate lamina is disposed closer to a wearer than is the second substrate lamina when the garment is worn. In some garments, the topsheet is disposed on the folded layers.

In some garments, the laminate is a first laminate, the channel is a main channel, and the garment comprises a second laminate disposed on the base layer and within the main channel. For some of those garments, a longitudinally-extending side channel is defined between the second laminate and each of the folded layers. The second laminate, in some garments, has an absorbent lamina and a first substrate lamina. In some garments, the absorbent lamina of the second lamina comprises SAP and, optionally, the first substrate lamina comprises tissue. In some garments, the second laminate comprises a second substrate lamina wherein, optionally, the absorbent lamina is disposed between the first and second substrate laminae. In some of those garments, the second substrate lamina comprises a nonwoven. In some garments, the nonwoven of the second substrate lamina of the first laminate has a first basis weight, the nonwoven of the second substrate lamina of the second laminate has a second basis weight, and the first basis weight is at least 10% more than the second basis weight. In some garments, the first laminate has a thickness at least 10% larger than a thickness of the second laminate such that the second laminate is recessed within the main channel relative to the folded layers.

In some garments, the dryness layer comprises a nonwoven sheet. In some garments, the nonwoven sheet comprises a through-air bonded polymer nonwoven. In some garments, the nonwoven sheet has a basis weight between 60 and 80 gsm. In some garments, the nonwoven sheet spans a lateral width of the dryness layer. For some garments, the dryness layer includes two or more longitudinally-extending strips coupled to the nonwoven sheet. In some garments, the strips are disposed between the absorbent core and the nonwoven sheet such that the nonwoven sheet is disposed closer to a wearer than are the strips when the garment is worn. In some garments, each of the strips includes an absorbent lamina disposed between first and second substrate laminae. For some of those garments, the absorbent lamina of each of the strips comprises SAP. The SAP of the absorbent lamina, for some garments, has a basis weight between 180 and 220 gsm. In some garments, the first and/or second substrate laminae of each of the strips comprise a nonwoven or tissue (which tissue is, in some of those garments, creped). In some garments, for each of the strips the tissue of each of the first and second substrate laminae has a basis weight between 14 and 20 gsm.

In some garments, the two or more strips include three or more strips that are spaced laterally apart along a width of the dryness layer such that a longitudinally-extending channel is defined between a first one of the strips and each of a second one of the strips and a third one of the strips. The three or more strips, in some garments, comprise four or more strips such that a longitudinally-extending channel is defined between the third strip and a fourth one of the strips. In some garments, each of the strips has a lateral width, the width of the first strip at least 10% larger, optionally between 90% and 110% larger, than the width of each of the second and third strips. In some garments, the lateral width of each of the second and third strips is between 10 and 15 mm. In some garments, the lateral width of the first strip is between 20 and 30 mm. In some garments, each of the channels has a lateral width that is within 10% of each of the second and third strips. The lateral width of each of the channels, in some garments, is between 10 and 15 mm.

In some garments, the dryness layer comprises a nonwoven sheet. In some garments, the nonwoven sheet comprises a through-air bonded polymer nonwoven. In some garments, the nonwoven sheet has a basis weight between 60 and 80 gsm. In some garments, the nonwoven sheet spans a lateral width of the dryness layer. For some garments, the dryness layer includes two or more longitudinally-extending strips coupled to the nonwoven sheet. In some garments, the strips are disposed between the absorbent core and the nonwoven sheet such that the nonwoven sheet is disposed closer to a wearer than are the strips when the garment is worn. In some garments, each of the strips includes an absorbent lamina disposed between first and second substrate laminae. For some of those garments, the absorbent lamina of each of the strips comprises SAP. The SAP of the absorbent lamina, for some garments, has a basis weight between 180 and 220 gsm. In some garments, the first and/or second substrate laminae of each of the strips comprise tissue which, in some of those garments, is creped. In some garments, for each of the strips the tissue of each of the first and second substrate laminae has a basis weight between 14 and 20 gsm.

In some garments, the two or more strips include three or more strips that are spaced laterally apart along a width of the dryness layer such that a longitudinally-extending channel is defined between a first one of the strips and each of a second one of the strips and a third one of the strips. The three or more strips, in some garments, comprise four or more strips such that a longitudinally-extending channel is defined between the third strip and a fourth one of the strips. In some garments, each of the strips has a lateral width, the width of the first strip at least 10% larger, optionally between 90% and 110% larger, than the width of each of the second and third strips. In some garments, the lateral width of each of the second and third strips is between 10 and 15 mm. In some garments, the lateral width of the first strip is between 20 and 30 mm. In some garments, each of the channels has a lateral width that is within 10% of each of the second and third strips. The lateral width of each of the channels, in some garments, is between 10 and 15 mm.

In some garments with two strips of the laminate, the strips are spaced laterally apart along a width of the dryness layer such that a longitudinally-extending channel is defined between a first one of the strips and a second one of the strips. In some garments, each of the two strips has a lateral width that is equal to a lateral width of the other one of the two strips. In some garments, the lateral width of each of the two strips is between 15 and 30 mm, for example between 15 and 25 mm, between 17 and 23 mm (e.g., equal to 20 mm), and/or between 20 and 25 mm (e.g., equal to 22 mm). In some garments, the dryness layer and/or the nonwoven sheet has a width of between 50 and 100 mm, between 60 and 90 mm, and/or between 70 and 80 mm (e.g., equal to 75 mm). In some garments, the two strips of laminate are spaced apart by a lateral distance that is greater than a width of either of the two strips; for example, a lateral distance of between 25 and 50 mm, between 30 and 45 mm, between 30 and 40 mm (e.g., equal to 35 mm), and/or between 30 and 35 mm (e.g., 31 mm).

Some of the present garments comprise: a chassis, an absorbent core, and a dryness layer. In some garments, the chassis has opposing front and rear waist portions, a crotch portion extending longitudinally between the front and rear waist portions, a topsheet, and a backsheet. In some garments, the absorbent core is coupled to the crotch portion. In some garments, the dryness layer extends longitudinally along the absorbent core and comprises: a nonwoven sheet; and two or more longitudinally-extending laminate strips coupled to the nonwoven sheet, each including an absorbent lamina disposed between first and second substrate laminae, the absorbent lamina comprising superabsorbent polymer (SAP) and the first and second substrate laminae each comprising tissue or nonwoven. In some garments, the strips are spaced apart laterally along a width of the dryness layer such that a longitudinally-extending channel is defined between a first one of the strips and a second one of the strips. In some garments, the absorbent core and the dryness layer are disposed between the topsheet and the backsheet.

In some garments, the two or more strips includes first and second strips of equal lateral widths. In some garments, the channel has a lateral width that equal to or greater than a width of each of the first and second strips. In some garments, a lateral width of the channel is between 10 and 40 millimeters (mm). In some garments, a lateral width of each of the first and second strips is between 12 and 24 millimeters (mm). In some garments, the two or more strips includes a third strip with a lateral width that is at least 10% larger than the width of each of the first and second strips. In some garments, a lateral width of the third strip is between 20 and 30 millimeters (mm).

In some garments, the width of the dryness layer is between 65 and 85 millimeters (mm). In some garments, the dryness layer has a longitudinal length between 185 and 270 millimeters (mm). In some garments, the absorbent core has a lateral width at least 10% larger than the width of the dryness layer; and/or the absorbent core and the dryness layer each have a longitudinal length, the length of the absorbent core at least 10% larger than the length of the dryness layer.

In some garments, for each of the strips the SAP of the absorbent lamina has a basis weight between 40 and 220 grams per square meter (gsm). In some garments, for each of the strips the tissue or nonwoven of each of the first and second substrate laminae has a basis weight between 10 and 20 gsm and, optionally, the tissue is creped. In some garments, the nonwoven sheet has a basis weight between 40 and 80 grams per square meter (gsm). In some garments, the nonwoven sheet comprises a through-air bonded polymer nonwoven. In some garments, the strips are disposed between the absorbent core and the nonwoven sheet such that the nonwoven sheet is disposed closer to a wearer than are the strips when the garment is worn.

The term "coupled" is defined as connected, although not necessarily directly, and not necessarily mechanically; two items that are "coupled" may be unitary with each other. The terms "a" and "an" are defined as one or more unless this disclosure explicitly requires otherwise. The term "substantially" is defined as largely but not necessarily wholly what is specified—and includes what is specified; e.g., substantially 90 degrees includes 90 degrees and substantially parallel includes parallel—as understood by a person of ordinary skill in the art. In any disclosed embodiment, the term "substantially" may be substituted with "within [a percentage] of" what is specified, where the percentage includes 0.1, 1, 5, and 10 percent.

The terms "comprise" and any form thereof such as "comprises" and "comprising," "have" and any form thereof such as "has" and "having," and "include" and any form thereof such as "includes" and "including" are open-ended linking verbs. As a result, an apparatus that "comprises," "has," or "includes" one or more elements possesses those one or more elements, but is not limited to possessing only those elements. Likewise, a method that "comprises," "has,"

or "includes" one or more steps possesses those one or more steps, but is not limited to possessing only those one or more steps.

Any embodiment of any of the apparatuses, systems, and methods can consist of or consist essentially of—rather than comprise/include/have—any of the described steps, elements, and/or features. Thus, in any of the claims, the term "consisting of" or "consisting essentially of" can be substituted for any of the open-ended linking verbs recited above, in order to change the scope of a given claim from what it would otherwise be using the open-ended linking verb.

Further, a device or system that is configured in a certain way is configured in at least that way, but it can also be configured in other ways than those specifically described.

The feature or features of one embodiment may be applied to other embodiments, even though not described or illustrated, unless expressly prohibited by this disclosure or the nature of the embodiments.

Some details associated with the embodiments described above and others are described below.

BRIEF DESCRIPTION OF THE DRAWINGS

The following drawings illustrate by way of example and not limitation. For the sake of brevity and clarity, every feature of a given structure is not always labeled in every figure in which that structure appears. Identical reference numbers do not necessarily indicate an identical structure. Rather, the same reference number may be used to indicate a similar feature or a feature with similar functionality, as may non-identical reference numbers. Views in the figures are drawn to scale, unless otherwise noted, meaning the sizes of the depicted elements are accurate relative to each other for at least the embodiment in the view.

FIG. 3B is not necessarily to scale.

FIG. 3C is not necessarily to scale.

FIG. 4 is not necessarily to scale.

FIG. 5B is not necessarily to scale.

FIG. 5B is not necessarily to scale.

DETAILED DESCRIPTION OF ILLUSTRATIVE EMBODIMENTS

Figure 1A:
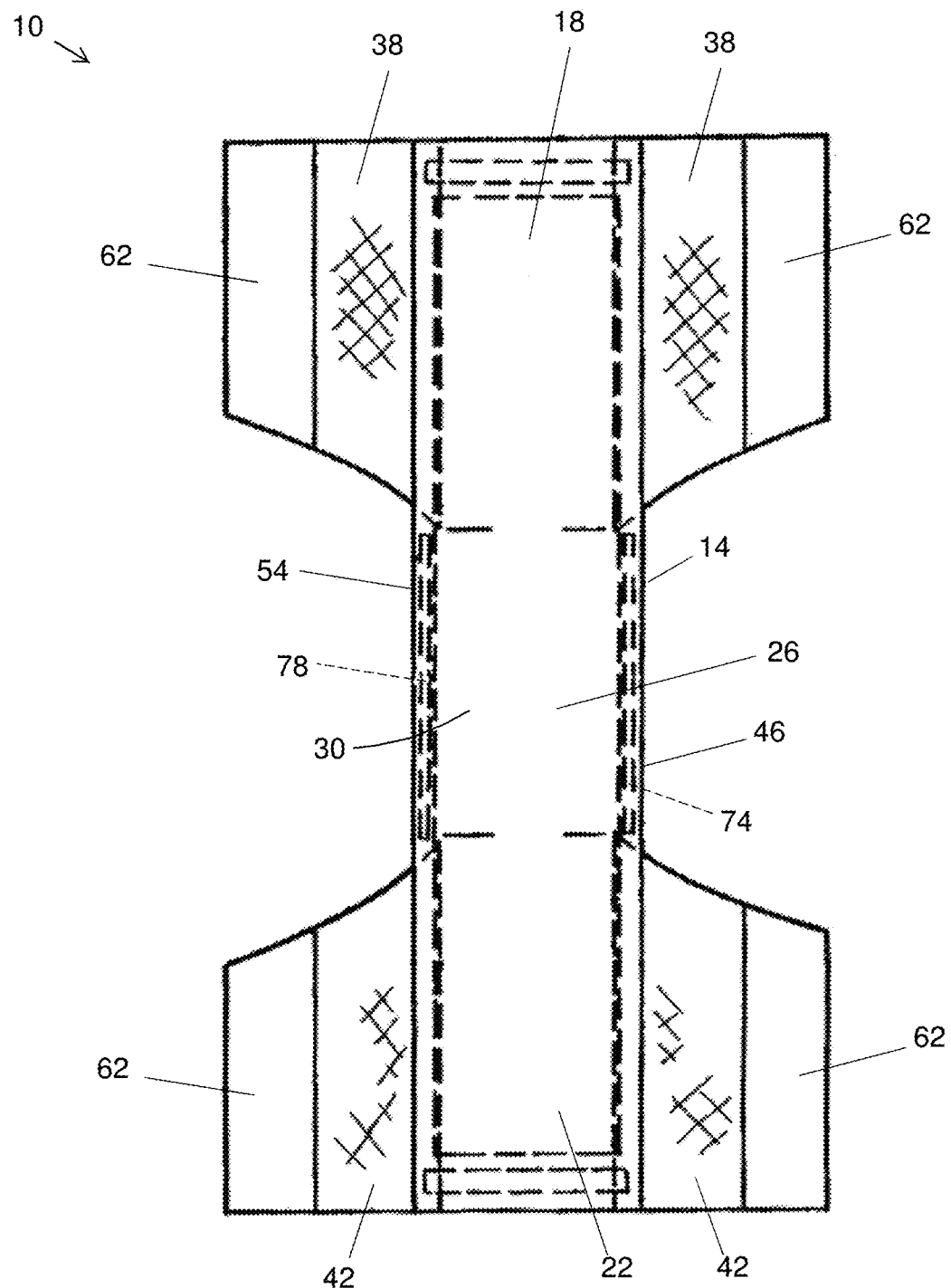
FIG. 1A is a bottom plan view of a prior art disposable absorbent article, specifically adult protective underwear, in an open configuration.
Figure 1B:
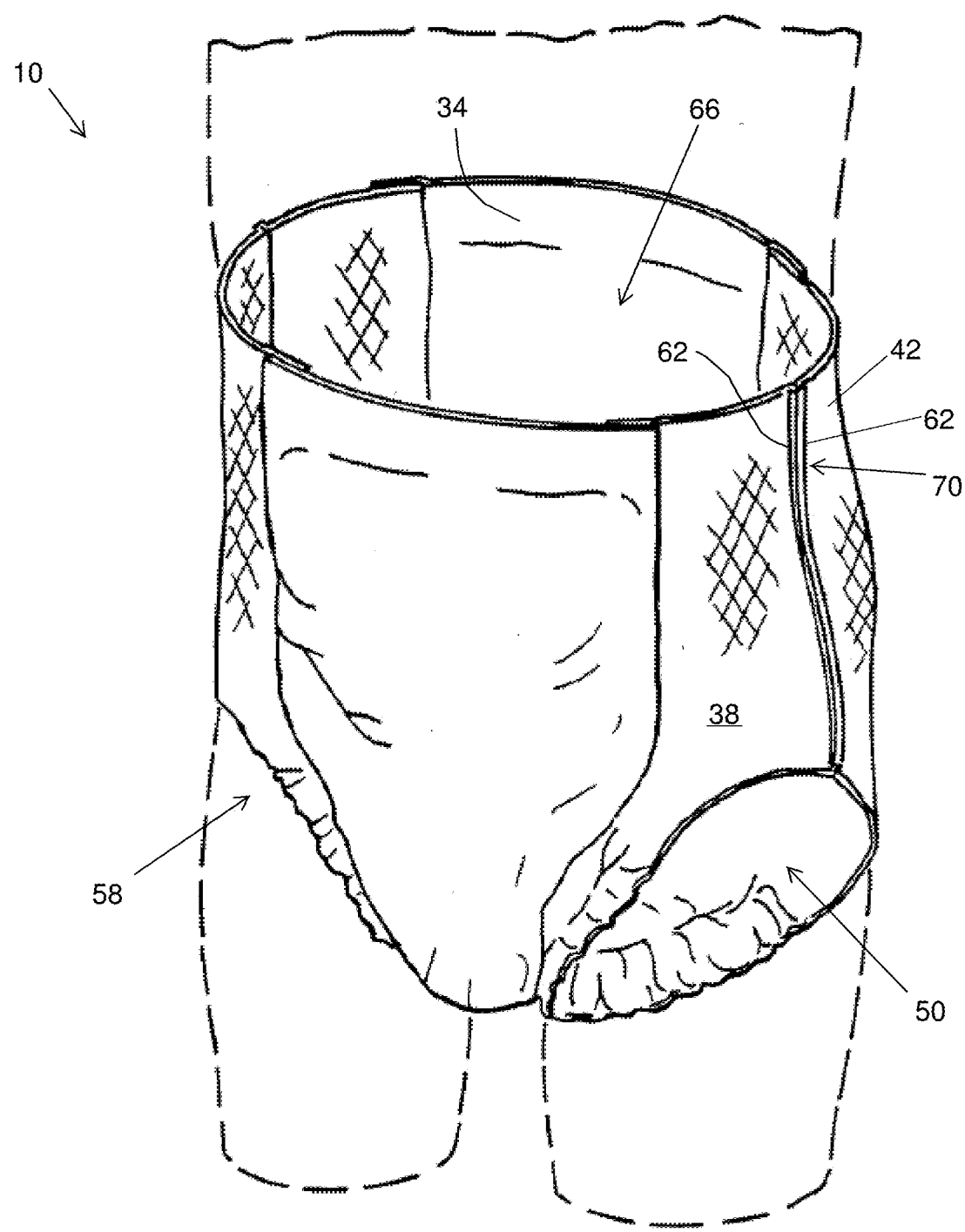
FIG. 1B is a perspective view of the protective underwear of FIG. 1A in a closed configuration.
Figure 2A:
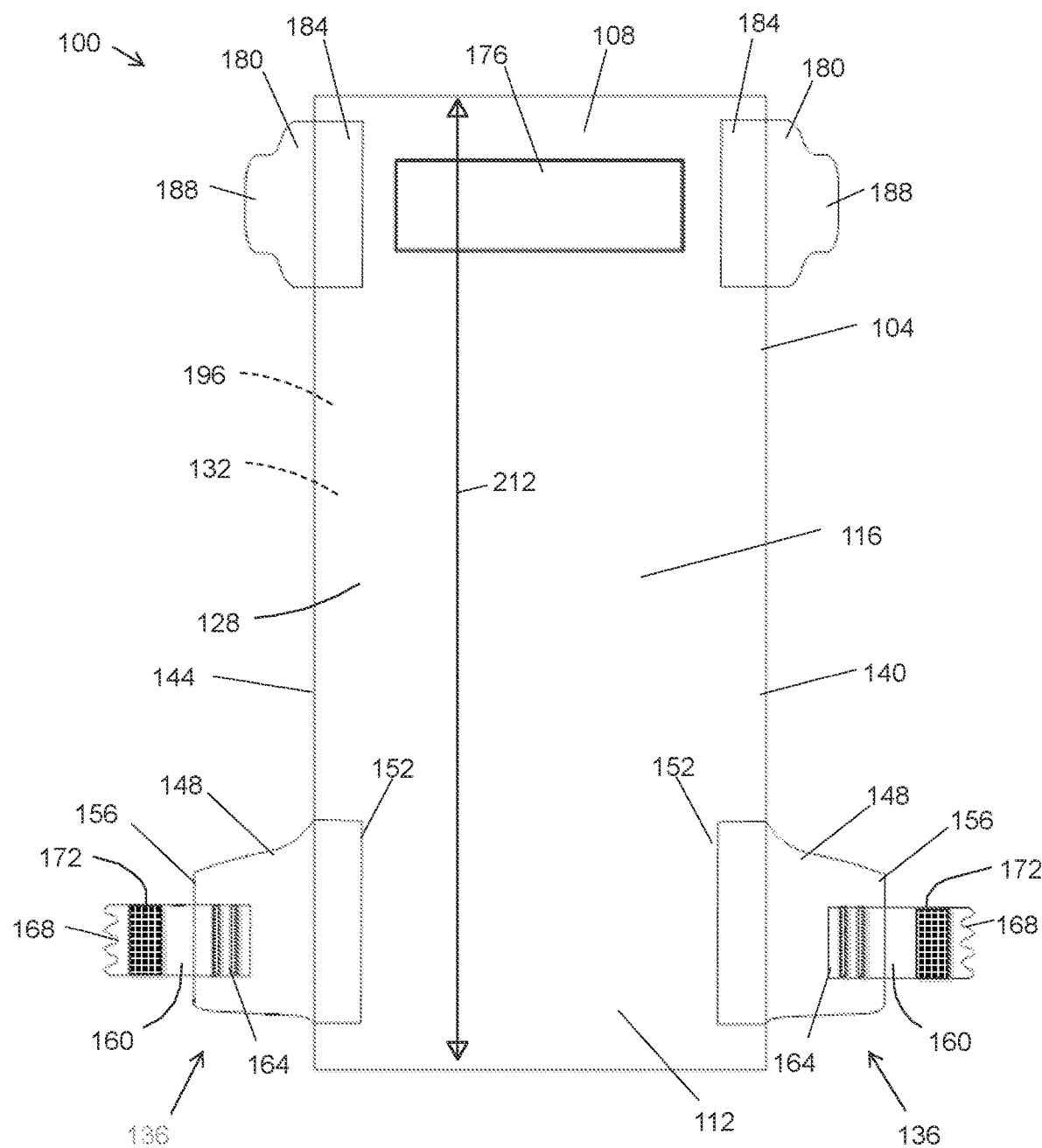
FIG. 2A is a bottom plan view of a prior art disposable absorbent article, specifically an adult incontinence brief, in an open configuration.
Figure 2B:
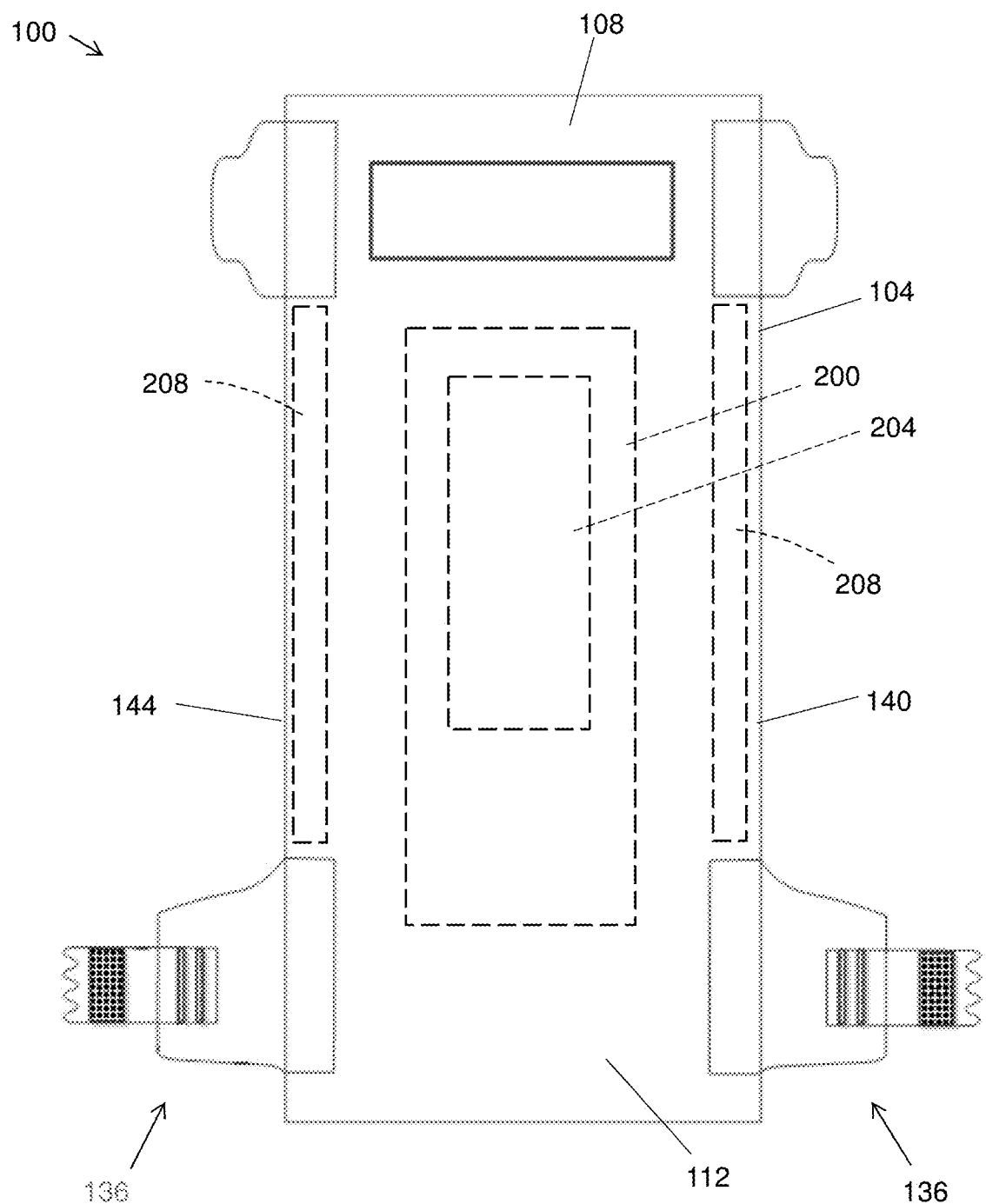
FIG. 2B is a bottom plan view of the brief of FIG. 2A, in an open configuration, showing certain internal components of the brief.
Figure 3A:
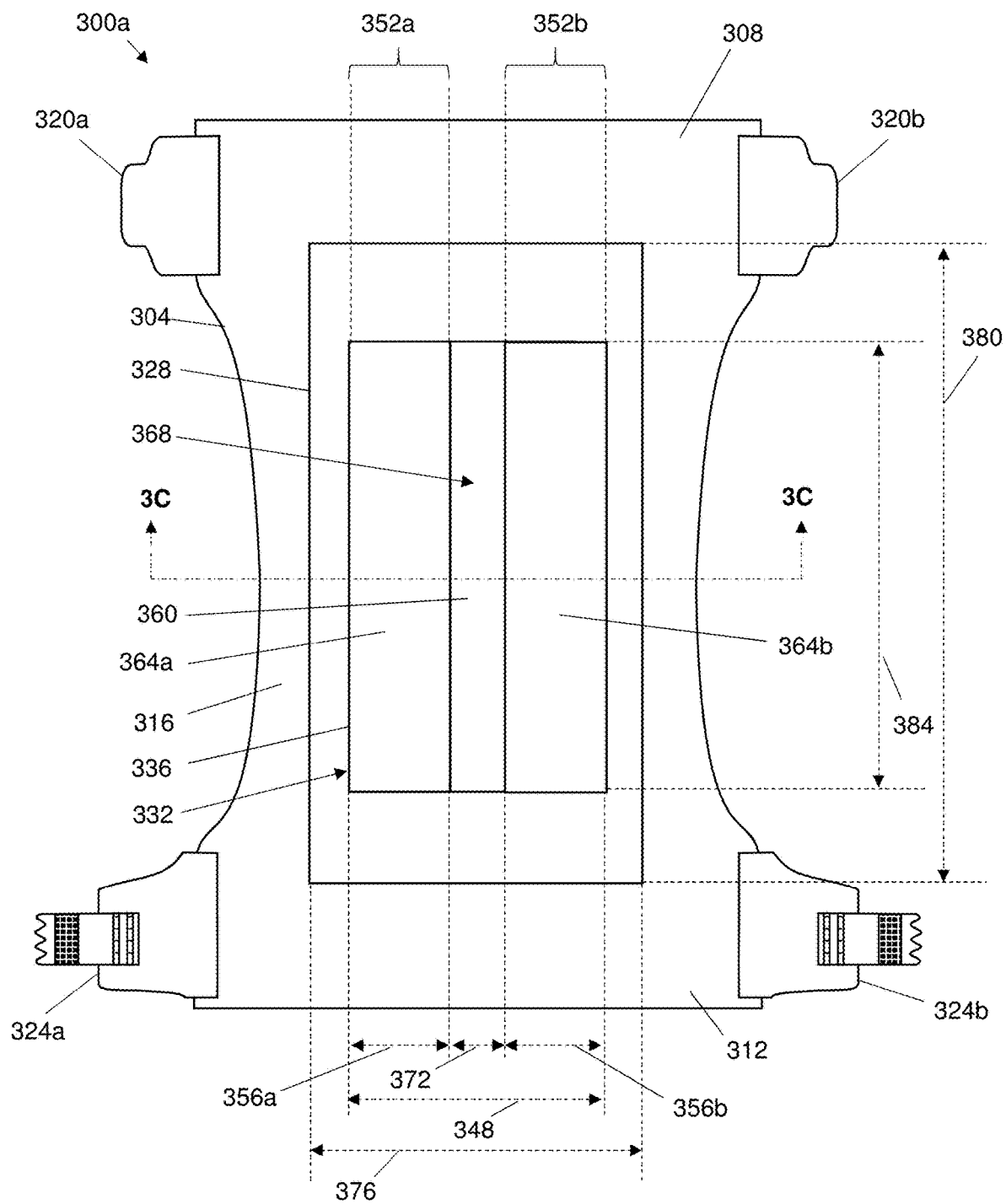
FIG. 3A is a top plan view of a first embodiment of the present absorbent garments, showing a dryness layer comprising a folded laminate disposed on an absorbent core. For clarity, a topsheet of the garment is not shown.
Figure 3B:
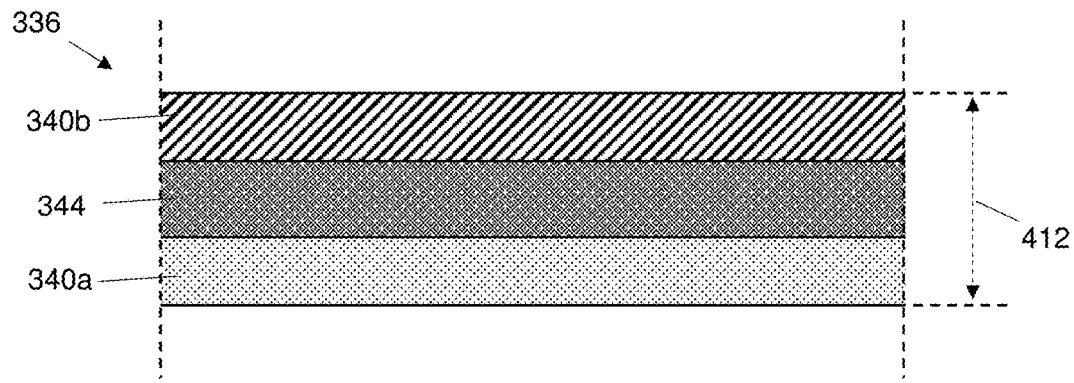
FIG. 3B is an exaggerated partial sectional view of a laminate suitable for use in the dryness layer of the garment of FIG. 3A.
Figure 3C:
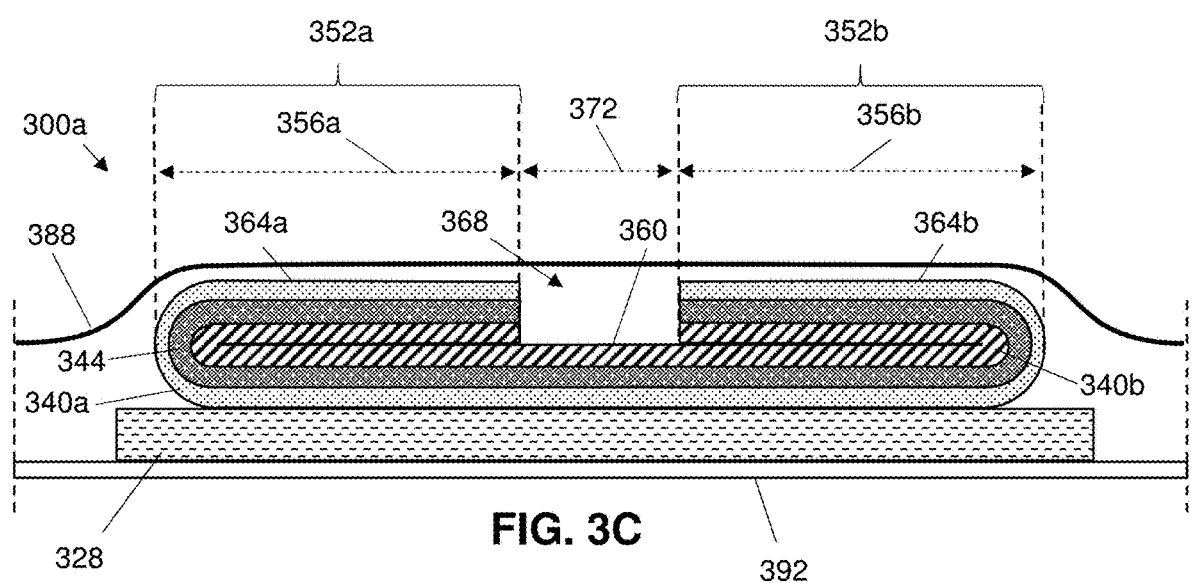
FIG. 3C is an exaggerated partial sectional view of the garment of FIG. 3A taken along line 3C-3C and illustrating the folded construction and resulting channel of the garment's dryness layer.

Referring to FIGS. 3A-3C, shown is an embodiment 300a of the present absorbent garments. Garment 300a can be a baby diaper, training pant, adult incontinence brief or underwear, bladder control pad, feminine hygiene pad, or the like, and comprises a chassis 304. Chassis 304 has a crotch portion 316 that extends longitudinally between a front waist portion 308 and a rear waist portion 312. Front waist portion 308 and rear waist portion 312 can each include ears and/or fasteners such that the front waist portion has first and second ends 320a and 320b configured to be coupled to first and second ends 324a and 324b, respectively, of the rear waist portion. When first ends 320a, 324a and second ends 320b, 324b are so coupled, garment 300a can define a closed configuration in which the garment is wearable. For example, in the closed configuration, front and rear waist portions 308 and 312 can cooperate to encircle and define a waist opening, a left side of chassis 304 can define a first leg opening, and a second side of the chassis can define a second leg opening.

Garment 300a can include an absorbent core 328 coupled to crotch portion 316. Core 328 can comprise any material or combination of materials suitable for absorbing liquids, such as, for example, a mixture of conventional fluff and superabsorbent polymer (SAP) particles. "Superabsorbent" or "superabsorbent material" or "SAP" refers to a water-swellable, water-insoluble organic or inorganic material capable, under the most favorable conditions, of absorbing at least about 15 times its weight in an aqueous solution containing 0.9 weight percent sodium chloride and, more desirably, at least about 30 times its weight in an aqueous solution containing 0.9 weight percent sodium chloride and, even more desirably, at least about 50 times its weight in an aqueous solution containing 0.9 weight percent sodium chloride.

Garment 300a includes a dryness layer 332 coupled to and extending longitudinally along core 328. Dryness layer 332 can have a structure configured to facilitate liquid acquisition and retention, thereby promoting comfort for a wearer. For example, dryness layer 332 can comprise a laminate 336 having an absorbent lamina 344 disposed between first and second substrate laminae 340a and 340b. The materials used for substrate lamina(e) (e.g., 340a and 340b) and absorbent lamina(e) (e.g., 344) can promote dryness at the wearer-facing surface of garment 300a by retaining liquid and/or transferring liquid to absorbent core 328.

Absorbent lamina 344 can comprise SAP particles and, in some embodiments, the SAP particles can be disposed within a matrix of adhesive material. For example, absorbent lamina 344 can comprise at least 90% (e.g., greater than 96% or 97%), by weight, SAP and less than or equal to 10% (e.g., less than 3% or 4%), by weight, adhesive. Suitable adhesive material can include, for example, a thermoplastic hot-melt adhesive composition or a pressure-sensitive thermoplastic adhesive composition. SAP, due to its absorbency, can retain liquid and thereby prevent the liquid from migrating to the wearer-facing surface of garment 300*a*. SAP swells when it absorbs liquid, which can impede liquid distribution and/or delivery to core 328 (referred to as "gel blocking"). The selection of SAP having appropriate permeability—determined at least in part by, for example, particle size, basis weight, and/or SAP material—can facilitate liquid retention while permitting adequate liquid spreading. SAP suitable for absorbent lamina 344 can have a basis weight between 40 and 140 grams per square meter (gsm), such as, for example, a basis weight greater than or equal to, or between any two of, 40, 60, 80, 100, 120, 140, or more gsm (e.g., between 60 and 120 gsm). Preferably, substantially all of the SAP particles of absorbent lamina 344 have a diameter less than or equal to 500 micrometers ($\mu$m) to reduce the roughness of the absorbent lamina. For example, ones of the SAP particles in absorbent lamina 344 having a diameter greater than or equal to 500 $\mu$m can account for less than 10% (e.g., less than 3% or less than 0.2%) of the mass of the SAP particles. An illustrative SAP suitable for absorbent lamina 344 is HP500E from Sumitomo Seika Chemicals Co., Ltd. in Osaka, Japan. As used herein, particle diameter refers to the equivalent diameter of the particle if the particle is modelled as a sphere. When manufactured, laminate 336 can be calendered to flatten the SAP of absorbent lamina 344.

The above-described SAP of absorbent lamina 344 are provided by way of illustration, and not by way of limitation. Exemplary superabsorbent polymer material that can be used in the present garments can comprise any superabsorbent polymer particles known from superabsorbent literature, for example such as described in Modern Superabsorbent Polymer Technology, F. L. Buchholz, A. T. Graham, Wiley 1998. For example, the SAP particles may be spherical, spherical-like or irregularly shaped particles, such as sausage shaped particles, or ellipsoid shaped particles of the kind typically obtained from inverse phase suspension polymerizations. The SAP particles can also be optionally agglomerated at least to some extent to form larger irregular particles. In some embodiments, the SAP particles can also have a surface modification, such as a partial or full surface coating, for example to increase the hydrophilicity of the SAP particles.

The SAP materials can be natural, synthetic and modified natural polymers and materials. In addition, the SAP materials can be or include organic compounds such as cross linked polymers. "Cross-linked" is a commonly understood term and refers to any approach for effectively rendering normally water-soluble materials substantially water insoluble, but swellable. Such polymers can include, for example, carboxymethylcellulose, alkali metal salts of polyacrylic acids, polyacrylamides, polyvinyl ethers, hydroxypropyl cellulose, polyvinyl morpholinone, polymers and copolymers of vinyl sulfonic acid, polyacrylates, polyacrylamides, polyvinyl pyridine and the like. Other suitable polymers include hydrolyzed acrylonitrile grafted starch, acrylic acid grafted starch, and isobutylene maleic anhydride copolymers, and mixtures thereof. Organic high-absorbency materials can include natural materials, such as agar, pectin, guar gum and peat moss. In addition to organic materials, superabsorbent materials may also include inorganic materials, such as absorbent clays and silica gels. Suitable examples of SAP include T9030, T9600, T9900, and Saviva polymers from BASF Corporation in Charlotte, N.C.; and W211, W112A, W125, S125D, QX-W1482, QX-W1486, QX-W1504, and QX-W1505 from Nippon Shokubai Co. Ltd, N.A.I.I. in Houston, Tex.; and AQUA KEEP SA50 II, SA55SX II, SA60N II, SA65s, HP500, HP600, and HP 700E from Sumitomo Seika Chemicals Co., Ltd. in Osaka, Japan. In some embodiments, the SAP can have a centrifuge retention capacity of 20-60 grams per gram (g/g), for example 30-50 g/g, and/or a particle size distribution (PSD) with most or substantially all particles having a diameter between 150 $\mu$m and 850 $\mu$m. In some embodiments, the SAP can have a centrifuge retention capacity between 33 and 38 g/g, or alternatively between 44 and 48 g/g.

Each of first and second substrate laminae 340*a* and 340*b* can be constructed from a nonwoven material and/or tissue to promote liquid acquisition and distribution to absorbent lamina 344 and absorbent core 328, thereby mitigating gel blocking. "Nonwoven" fabrics, according to an INDA definition, are broadly defined as sheet or web structures bonded together by entangling fiber or filaments, and by perforating films, mechanically, thermally, or chemically. They are flat, porous sheets that are made directly from separate fibers or from molten plastic or plastic film. They are not made by weaving or knitting and do not require converting the fibers to yarn. The basis weight of nonwoven fabrics is usually expressed as gsm or grams per square meter. Suitable nonwoven materials can include, for example, spunbond, spunlace, or carded webs of one or more polymers, including polypropylene, polyethylene, nylon, polyester, and blends of these materials. When constructed from a nonwoven, a substrate lamina can have a basis weight of at least 30 gsm, such as, for example, a basis weight greater than or equal to, or between any two of, 30, 40, 50, 60, 70, 80, 90, 100, 110, 120, 130, or more gsm (e.g., between 40 and 50 gsm, or 45 gsm). Suitable tissues can include, for example, porous tissues, creped tissues, and standard tissues. When constructed from tissue, a substrate lamina can have a basis weight of at least 10 gsm, such as, for example, a basis weight greater than or equal to, or between any two of, 10, 12, 14, 16, 18, 20, 22, 24, 26, 28, 30, or more gsm (e.g., between 14 and 20 gsm, or 17 gsm).

As shown, first substrate lamina 340*a* comprises a dry-creped tissue having a basis weight between 14 and 20 gsm (e.g., 17 gsm), and second substrate lamina 340*b* comprises a resin-bonded polyester fiber nonwoven having a basis weight between 40 and 50 gsm (e.g., 45 gsm). First substrate lamina 340*a* can thereby provide a capillary network through which liquid is spread throughout laminate 336 to absorbent lamina 344 and/or absorbent core 328. Second substrate lamina 340*b*, due at least in part to its nonwoven construction, can absorb and distribute rapid insults of liquid to further promote liquid distribution and acquisition such that leakage is reduced. An illustrative tissue suitable for first substrate lamina 340*a* is a 17-gsm 3995 Machine Creped tissue from Dunn paper. An illustrative nonwoven suitable for second substrate lamina 340*b* is Fitesa Carded Resin Bond, available from Fitesa in Simpsonville, S.C.

In other embodiments, laminate 336 can have any suitable number of substrate and absorbent laminae arranged in any suitable order, such as, for example, greater than or equal to or between any two of 1, 2, 3, 4, 5, 6, 7, 8, or more substrate laminae (e.g., 340*a* and 340*b*) and greater than or equal to or between any two of 1, 2, 3, 4, 5, 6, 7, 8, or more absorbent laminae (e.g., 344). For example, any two adjacent laminae in laminate 336 can be the same type of laminae (e.g., both can be substrate laminae or absorbent laminae) or laminae of different types (e.g., one can be one of the substrate lamina (e) and one can be one of the absorbent lamina(e)). Providing additional laminae can improve the liquid retention capacity of laminate 336.

In some embodiments, laminate 336 can have a thickness 412 that is at least 0.2 mm, such as, for example, a thickness that is greater than or equal to, or between any two of, 0.20, 0.25, 0.30, 0.35, 0.40, 0.45, 0.50, 0.55, 0.60, 0.65, 0.70, or more millimeters (e.g., between 0.4 and 0.5 mm).

Laminate 336 can be folded one or more times such that dryness layer 332 includes multiple laminate layers, including a base layer 360 and folded layers 364a and 364b disposed within longitudinally-extending edge regions 352a and 352b, respectively. Folded layers 364a and 364b can be layered on base layer 360, which can span a lateral width 348 of dryness layer 332. Folded layers 364a and 364b can each span less than half of width 348 such that a longitudinally-extending channel 368 is defined between the folded layers. For example, each of edge regions 352a and 352b can have a width (e.g., 356a and 356b, respectively) that spans less than or equal to, or between any two of, 50%, 40%, 30%, 20%, or 10% (e.g., between 35% and 45%) of width 348. As a result, channel 368 can have a lateral width 372 that spans less than or equal to, or between any two of, 80%, 70%, 60%, 50%, 40%, 30%, 20%, or 10% (e.g., between 10% and 30%) of width 348. For example, width 372 can be greater than or equal to, or between any two of, 8, 12, 16, 20, 24, 28, or more millimeters (mm) (e.g., between 8 and 20 mm, between 8 and 12 mm, or 10 mm).

The folded construction of laminate 336 can promote comfort by improving liquid acquisition and retention. Folded layers 364a and 364b, at least by providing additional SAP within edge regions 352a and 352b, can contain liquid and thus better prevent liquid from migrating to the wearer-facing surface of garment 300a. First and second substrate laminae 340a and 340b can facilitate liquid transfer between the SAP of base layer 360 and the SAP of each of folded layers 364a and 364b. And dryness layer 332, at least by having channel 368, can provide adequate volume for the rapid acquisition and distribution of liquid to absorbent core 328. In other embodiments, dryness layer 332 can include any suitable number of folded layers (e.g., 364a and 364b) within each of edge regions 352a and 352b, such as, for example, greater than or equal to or between any two of 1, 2, 3, 4, 5, 6, 7, 8, or more folded layers. Providing multiple folded layers in each of edge regions 352a and 352b can enhance liquid containment within the edge regions.

As shown, dryness layer 332 can be disposed on top of absorbent core 328. For example, base layer 360 can be coupled to absorbent core 328 such that folded layers 364a and 364b are each disposed closer to a wearer than is the base layer when garment 300a is worn. In this arrangement, first substrate lamina 340a is configured to be disposed closer to a wearer than is second substrate lamina 340b within each of folded layers 364a and 364b, while the second substrate lamina is configured to be disposed closer to the wearer than is first substrate layer within base layer 360. Liquid can thereby readily pass through channel 368 for distribution to absorbent core 328 and retention within absorbent lamina 344. When first substrate lamina 340a is constructed from tissue, the capillary action of the tissue can distribute liquid to absorbent core 328 when liquid is first received within edge portions 352a and 352b, whereas second substrate lamina 340b, when constructed from a nonwoven, can rapidly acquire liquid within channel 368 and transfer liquid from each of folded layers 364a and 364b to base layer 360.

In other embodiments, dryness layer 332 can be disposed below absorbent core 328 such that the dryness layer can receive liquid from the absorbent core. For example, each of the folded layers 364a and 364b can be coupled to the bottom surface of absorbent core 328 such that the folded layers are configured to be disposed closer to a wearer than is base layer 360. In this arrangement, liquid can readily pass from absorbent core 328 to channel 368 and first substrate lamina 340a within folded layers 364a and 364b. In yet further embodiments, whether dryness layer 332 is disposed above or below absorbent core 328, the dryness layer can be coupled to the absorbent core such that base layer 360 is disposed closer to a wearer than are folded layers 364a and 364b when garment 300a is worn.

Chassis 304 can include a topsheet 388 configured to face a wearer during use of garment 300a (not shown in FIG. 3A, for clarity) and a backsheet 392. Absorbent core 328 and dryness layer 332 can be disposed between topsheet 388 and backsheet 392 such that, for example, the topsheet is disposed on folded layers 364a and 364b. Topsheet 388 can, but need not, follow the contour of channel 368 (e.g., the topsheet can be disposed on base layer 360 within the channel). Topsheet 388 can be liquid permeable, while backsheet 392 can be liquid-impermeable and can include, for example, an inner liquid-impermeable film and an outer nonwoven backsheet that can be a nonwoven fabric. A "film" is a membrane-like layer of material formed of one or more polymers, which does not have a form consisting predominately of a web-like structure of fibers and/or other fibers. Backsheet 392 can be breathable, for example, an inner liquid-impermeable film of backsheet 392 can comprise a breathable film. The terms "breathable," "breathable film," "breathable laminate" or "breathable outer cover material" or "breathable backsheet" refers to a film, laminate, or outer cover material having a water vapor transmission rate ("WVTR") of at least about 300 grams/m$^2$/24 hours. Breathable materials typically rely on molecular diffusion of vapor, and are substantially liquid impermeable. "Nonwoven backsheet" is a backing substrate layer in the outer cover; a nonwoven backsheet is most often a nonwoven layer facing away from the wearer.

Dryness layer 332 can be smaller than absorbent core 328. For example, absorbent core 328 can have a lateral width 376 that is at least 10% larger than width 348 of dryness layer 332, such as, for example, a lateral width that is at least or between any two of 10%, 20%, 30%, 40%, 50%, 60%, 70%, 80%, 90%, or 100% larger than width 348. Additionally, or alternatively, absorbent core 328 can have a longitudinal length 380 that is at least 10% larger than length 384 of dryness layer 332, such as, for example, a longitudinal length that is at least or between any two of 10%, 20%, 30%, 40%, 50%, 60%, 70%, 90%, or 100% larger than length 384. A larger absorbent core 328 provides additional absorption capacity for garment 300a, while permitting dryness layer 332 to be appropriately sized and positioned for liquid acquisition at or near the liquid insult point when the garment is worn. Dryness layer 332 can have, for example, a width 348 that is at least 50 mm, such as, for example, a width greater than or equal to or between any two of 50, 55, 60, 65, 70, 75, 80, 85, 90, 95, 100, or more millimeters (e.g., between 65 and 85 mm, or 75 mm), and a length 384 that is at least 170 mm, such as, for example, a length greater than or equal to or between any two of 170, 180, 190, 200, 210, 220, 230, 240, 250, 260, 270, 280, or more millimeters (e.g., between 185 and 270 mm). In other embodiments, however, dryness layer 332 can span substantially the same area as absorbent core 328 such that width 376 of the absorbent core is within 10% of width 348 and/or length 380 of the absorbent core is within 10% of length 384. In some embodiments, dryness layer 332 can be disposed closer to front waist portion 308 than to rear waist portion 312.

Figure 4:
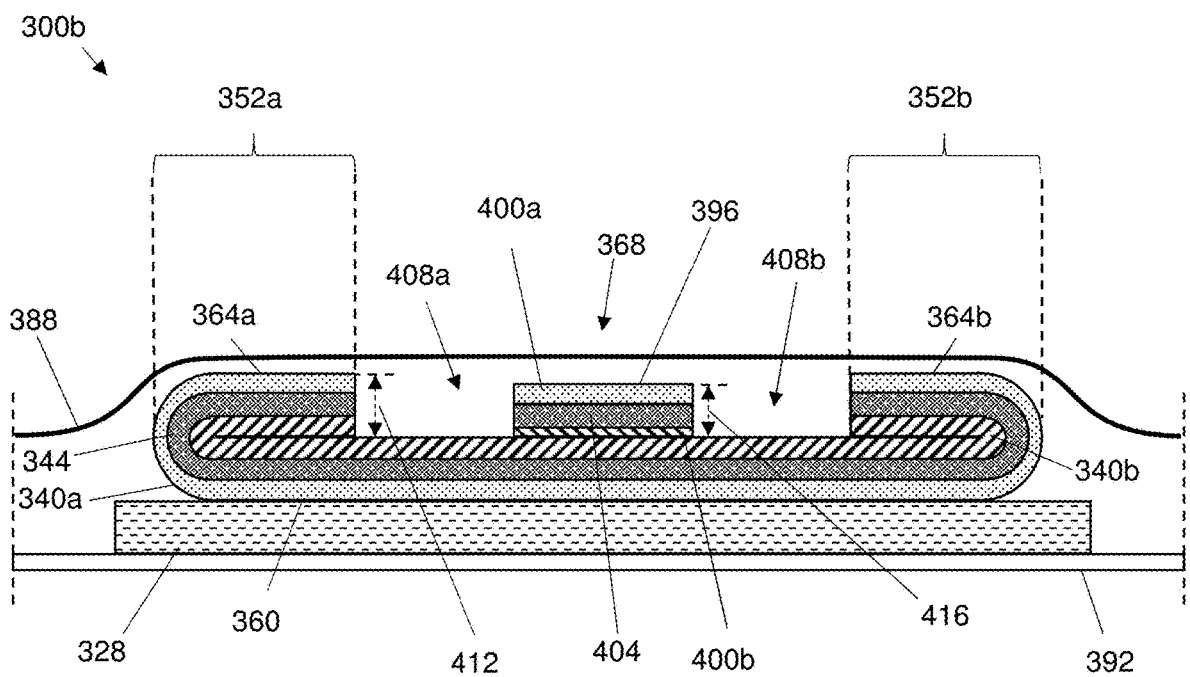
FIG. 4 is an exaggerated partial sectional view of a second embodiment of the present absorbent garments that is substantially similar to the garment of FIG. 3A, except for the inclusion of a middle laminate disposed within a channel of the garment.

Referring to FIG. 4, shown is another embodiment 300b of the present absorbent garments. Garment 300b can be substantially similar to garment 300a, with the primary exception being that garment 300b includes a middle laminate 396. Middle laminate 396 can be layered on base layer 360 within channel 368. Longitudinally-extending side channels 408a and 408b can be defined between middle laminate 396 and folded layers 364a and 364b, respectively. By defining multiple side channels 408a and 408b, dryness layer 332 can improve liquid acquisition. In other embodiments, dryness layer 332 can include multiple middle laminates (e.g., 396) layered on base layer 360 such that the dryness layer defines three or more side channels between the middle laminates and folded layers, such as, for example, greater than or equal to, or between any two of, 3, 4, 5, 6, 7, 8, or more side channels.

Middle laminate 396 can have a thickness 416 smaller than a thickness 412 of laminate 336 such that the middle laminate is recessed within channel 368 relative to folded layers 364a and 364b. For example, thickness 412 can be at least 10% larger than thickness 416, such as, for example, at least or between any two of 10%, 20%, 30%, 40%, 50%, 60%, 70%, or 80% larger than thickness 416. Topsheet 388 can, but need not, conform to the depression defined by middle laminate 396 (e.g., topsheet 388 can be disposed on the upper surface of the middle laminate). Providing a recessed middle laminate 396 can promote fluid containment within folded layers 364a and 364b by directing fluid towards edge portions 352a and 352b.

Middle laminate 396 can include an absorbent lamina 404 comprising SAP disposed between first and second substrate laminae 400a and 400b, each comprising tissue and/or a nonwoven. As shown, first substrate lamina 400a can be configured to be disposed closer to a wearer than are absorbent lamina 404 and second substrate lamina 400b. First substrate lamina 400a and absorbent lamina 404 can, but need not, be substantially similar to, respectively, first substrate lamina 340a and absorbent lamina 344 of laminate 336. Middle laminate 396 can achieve a thickness 416 smaller than thickness 412 by having a second substrate lamina 400b different from second substrate lamina 340b of laminate 336. For example, second substrate lamina 340b can comprise a nonwoven that has a basis weight at least 10% higher, such as, for example, at least or between any two of 10%, 20%, 30%, 40%, 50%, 60%, 70%, or 80% higher than the basis weight of a nonwoven of second substrate lamina 400b. Alternatively, middle laminate 396 can omit second substrate lamina 400b such that the middle laminate comprises at least one fewer lamina than laminate 336. In other embodiments, second substrate lamina 400b can be substantially similar to second substrate lamina 340b.

Figure 5A:
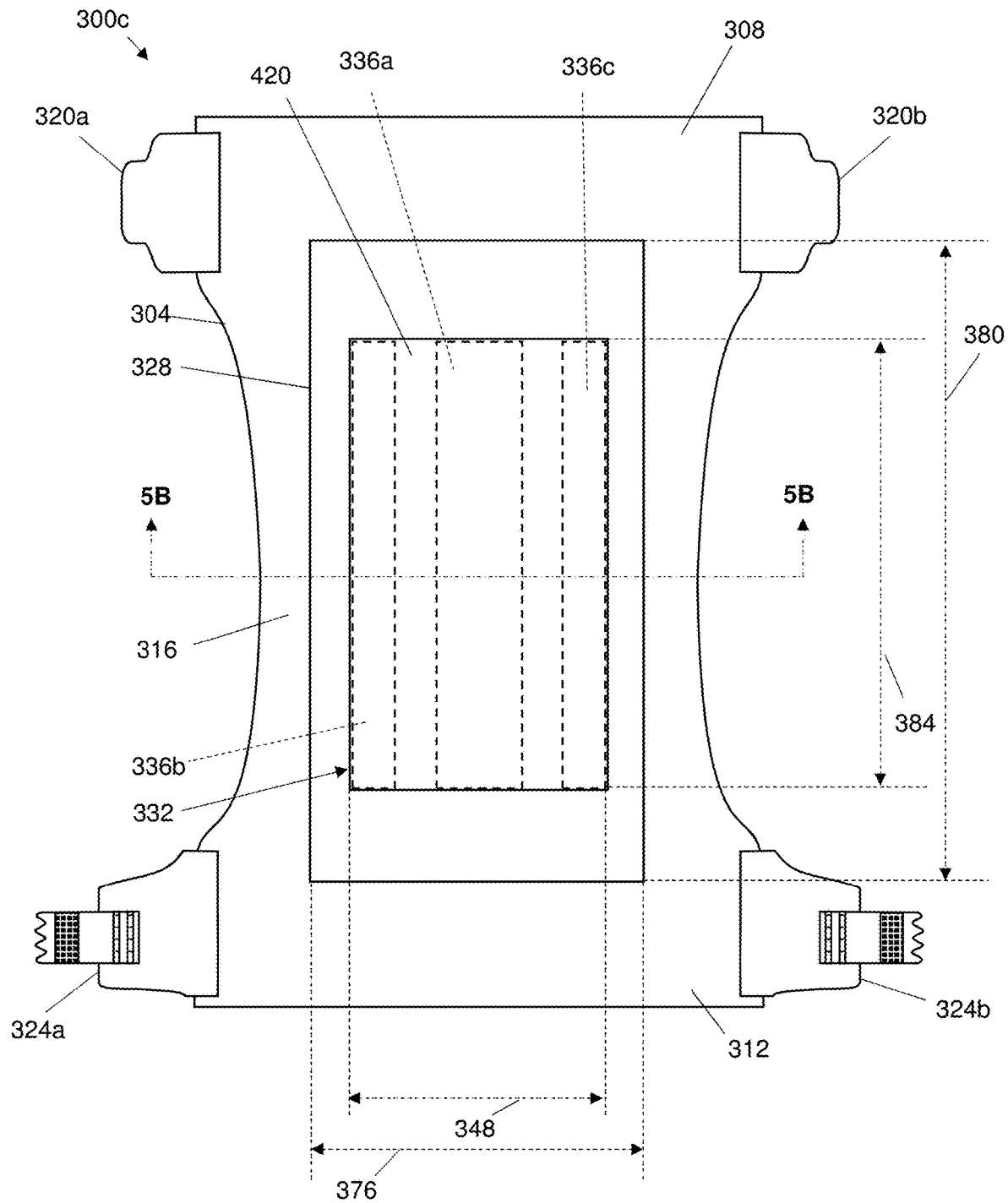
FIG. 5A is a top plan view of a third embodiment of the present absorbent garments, showing a dryness layer comprising a nonwoven sheet and three laminate strips disposed on an absorbent core. For clarity, a topsheet of the garment is not shown.
Figure 5B:
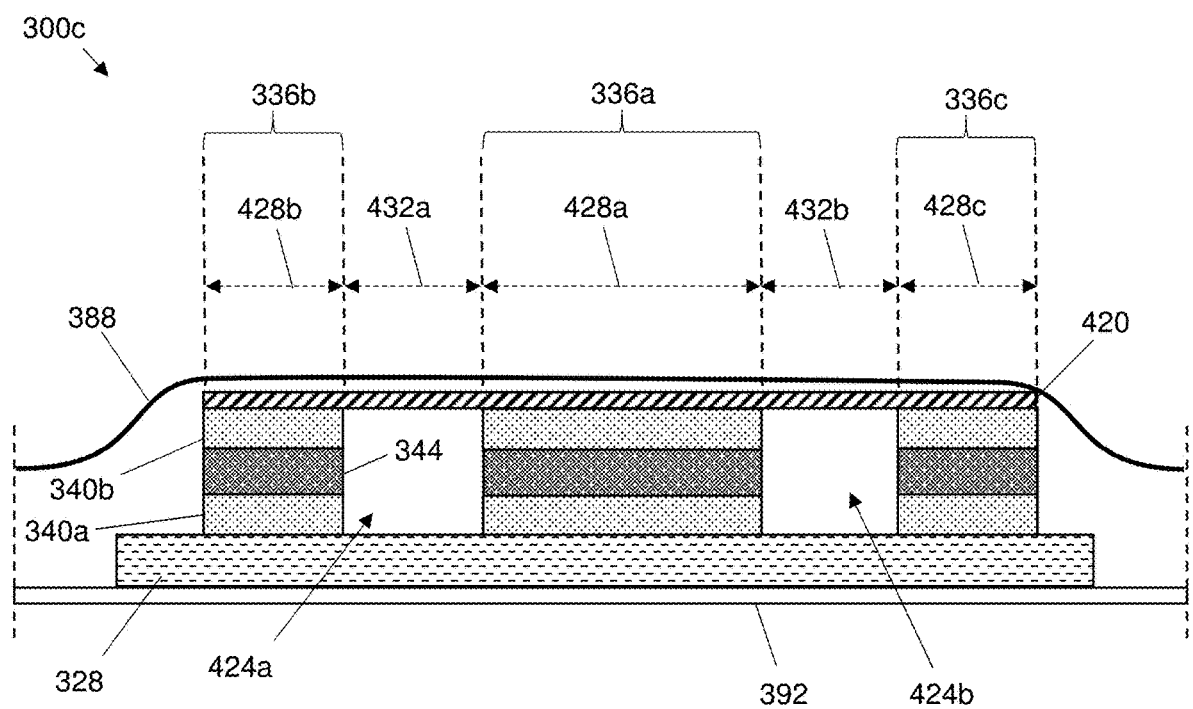
FIG. 5B is an exaggerated partial sectional view of the garment of FIG. 5A, taken along line 5B-5B and illustrating the spacing of the laminate strips and resulting channels of the garment's dryness layer.

Referring to FIGS. 5A and 5B, shown is another embodiment 300c of the present absorbent garments. Garment 300c can be substantially similar to garment 300a, the primary exception being the construction of dryness layer 332. Dryness layer 332 can comprise two or more longitudinally-extending laminate strips, for example each having a construction similar to laminate 336 of garment 300a. In the depicted configuration, dryness layer 332 comprises three longitudinally-extending laminate strips 336a-336c, each having a construction similar to laminate 336 of garment 300a. However, as shown, each of strips 336a-336c has first and second substrate laminae 340a and 340b that each comprise tissue or nonwoven. For example, first and second substrate laminae 340a and 340b can each comprise a dry-creped tissue having a basis weight between 14 and 20 gsm (e.g., 17 gsm). In other configurations, first and second substrate laminae 340a and 340b can each comprise a nonwoven. In yet further configurations, one of first and second substrate laminae 340a and 340b can comprise a nonwoven and the other of first and second substrate laminae 340a and 340b can comprise tissue (e.g., creped tissue, such as 17 gsm dry-creped tissue). Because strips 336a-336c are not folded, SAP suitable for the strips can have a higher basis weight than that used in laminate 336 of garment 300a. For example, each of strips 336a-336c can have an absorbent lamina 344 comprising SAP that has a basis weight of at least 150 grams per square meter, such as, for example, a basis weight greater than or equal to, or between any two of, 150, 170, 190, 210, 230, 250, or more gsm (e.g., between 180 and 220 gsm). An illustrative SAP suitable for use in strips 336a-336c is T9900 from BASF Corporation in Charlotte, N.C.

Dryness layer 332 can comprise a nonwoven sheet 420 coupled to strips 336a-336c. As shown, sheet 420 is disposed on strips 336a-336c such that the sheet is closer to a wearer than are the strips when garment 300c is worn. Sheet 420 can span width 348 of dryness layer 332, and can comprise a through-air bonded polymer (e.g., polyester) nonwoven having a basis weight of at least 50 gsm, such as, for example, a basis weight greater than or equal to, or between any two of, 50, 60, 70, 80, 90 or more gsm (e.g., between 60 and 80 gsm, or 70 gsm). Nonwoven sheet 420 can absorb and transfer rapid insults of liquid to strips 336a-336c and/or core 328 to reduce leakage.

First, second, and third strips 336a, 336b, and 336c are each spaced laterally along width 348 of dryness layer 332. For example, first strip 336a can be disposed between second and third strips 336b and 336c. First strip 336a can have a width 428a that is larger than the widths of second and third strips 336b and 336c (e.g., 428b and 428c, respectively). For example, width 428a can be at least 10% larger than each of widths 428b and 428c, such as, for example, a width that is at least or between any two of 10%, 30%, 50%, 70%, 90%, 110%, or 130% larger (e.g., between 90% and 110% larger, or 100% larger) than each of widths 428b and 428c. Additionally, or alternatively, second and third strips 336b and 336c can be substantially the same size (e.g., width 428b can be within 10% of width 428c). By way of illustration, first strip 336a can have a width 428a greater than or equal to, or between any two of, 16, 18, 20, 22, 24, 26, 28, 30, 32, 34, or more millimeters (e.g., between 20 and 30 mm, or 25 mm). By way of further illustration, each of second and third strips 336b and 336c can have a width (e.g., 428b and 428c, respectively) greater than or equal to, or between any two of, 6, 8, 10, 12, 14, 16, 18, or more millimeters (e.g., between 10 and 15 mm, or 12.5 mm). In some embodiments, width 428a can be substantially the same as widths 428b and 428c.

Longitudinally-extending channels 424a and 424b can be defined between first strip 336a and each of second and third strips 336b and 336c, respectively. Channels 424a and 424b can be appropriately sized to facilitate liquid acquisition. For example, widths 432a and 432b of channels 424a and 424b, respectively, can be substantially the same as (e.g., within 10% of) the widths of second and third strips 336b and 336c (e.g., 428b and 428c, respectively). By way of illustration, widths 432a and 432b can each be greater than or equal to, or between any two of, 6, 8, 10, 12, 14, 16, 18, or more millimeters (e.g., between 10 and 15 mm or 12.5 mm). Strips 336a-336c and channels 424a and 424b are sized such that dryness layer 332 comprises sufficient laminate material to retain and transfer insults of liquids to absorbent core 328 while providing adequate volume (e.g., via the channels) to promote improved liquid acquisition and reduce leakage.

In some embodiments, dryness layer 332 can comprise two or more laminate strips, such as, for example, greater than or equal to, or between any two of, 2, 3, 4, 5, 6, 7, 8, 9, 10, or more laminate strips, to define one or more channels between the strips, such as, for example, greater than or equal to, or between any two of, 1, 2, 3, 4, 5, 6, 7, 8, 9, or more channels. To illustrate, dryness layer 332 can comprise a fourth laminate strip such that a channel is defined between the third and fourth strips.

As shown, dryness layer 332 is disposed above absorbent core 328. For example, each of strips 336a-336c can be disposed on absorbent core 328 and, optionally, a topsheet 388 can be disposed on nonwoven sheet 420. In other embodiments, however, dryness layer 332 can be disposed below absorbent core 328. For example, absorbent core 328 can be disposed on nonwoven sheet 420 such that the nonwoven sheet receives liquid from the absorbent core and distributes the liquid to strips 336a-336c. In yet further embodiments, regardless of whether dryness layer 332 is disposed above or below absorbent core 328, the dryness layer can be coupled to the absorbent core such that strips 336a-336c are configured to be disposed closer to a wearer than is nonwoven sheet 420.

Figure 6A:
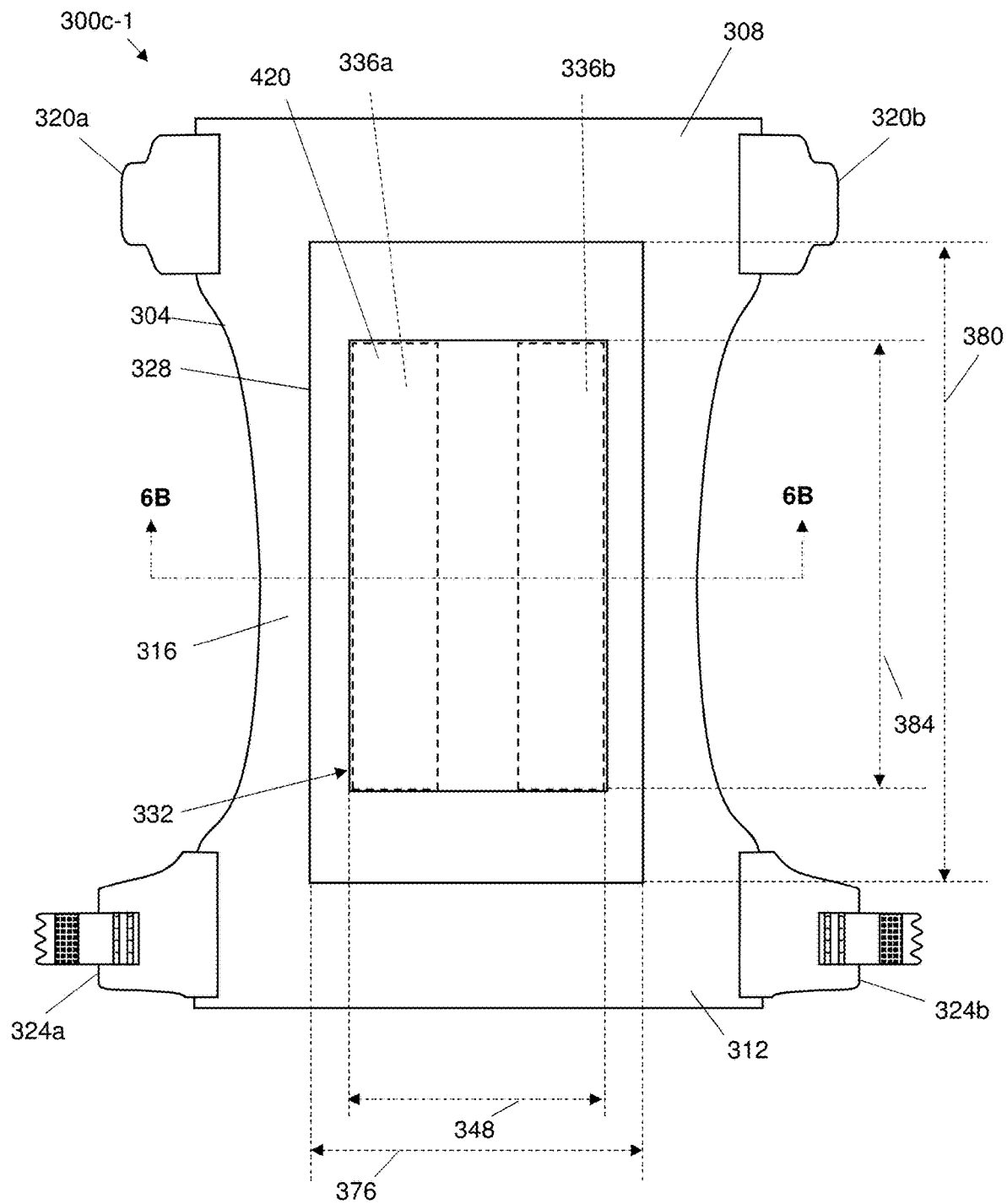
FIG. 6A is a top plan view of a fourth embodiment of the present absorbent garments, showing a dryness layer comprising a nonwoven sheet and two laminate strips disposed on an absorbent core. For clarity, a topsheet of the garment is not shown.
Figure 6B:
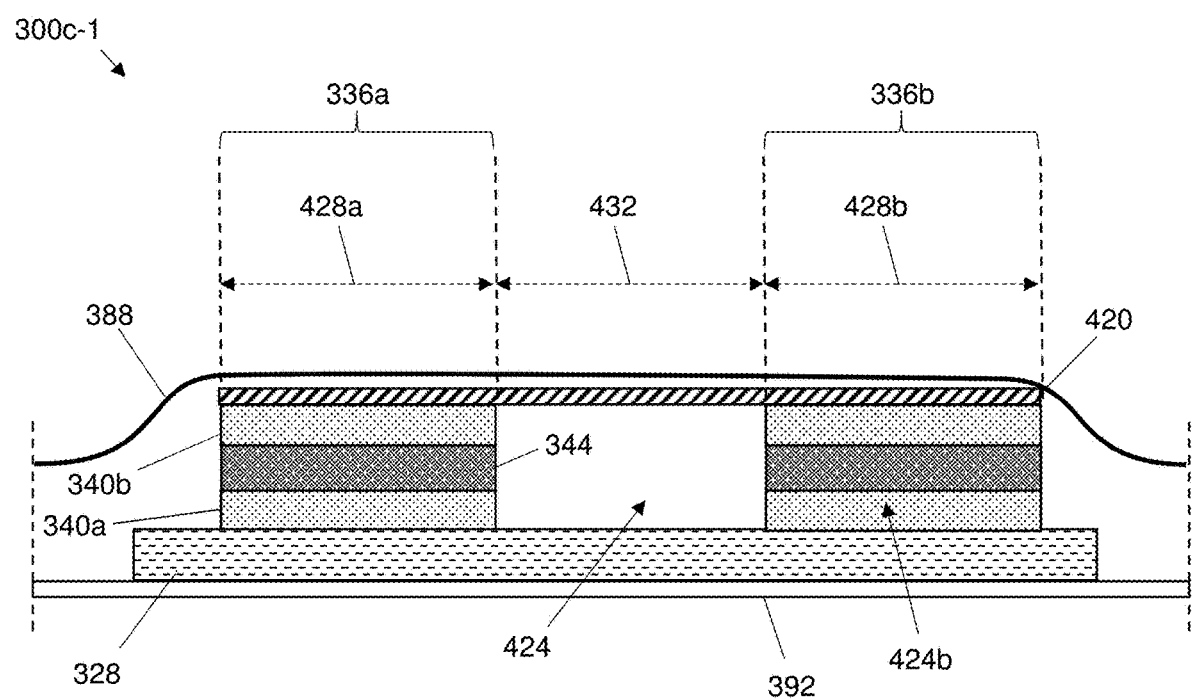
FIG. 6B is an exaggerated partial sectional view of the garment of FIG. 6A, taken along line 6B-6B and illustrating the spacing of the laminate strips and resulting channel of the garment's dryness layer.

Referring to FIGS. 6A and 6B, shown is another embodiment 300c-1 of the present absorbent garments. Garment 300c-1 can be substantially similar to garment 300c, the primary exception being the construction of dryness layer 332. In garment 300c-1, dryness layer 332 comprises two longitudinally-extending laminate strips 336a and 336b, each having a construction similar to laminate 336 of garment 300a. However, as shown, each of strips 336a and 336b has first and second substrate laminae 340a and 340b that each comprise tissue or nonwoven. For example, first and second substrate laminae 340a and 340b can each comprise a dry-creped tissue having a basis weight between 14 and 20 gsm (e.g., 17 gsm). In other configurations, first and second substrate laminae 340a and 340b can each comprise a nonwoven. In yet further configurations, one of first and second substrate laminae 340a and 340b can comprise a nonwoven and the other of first and second substrate laminae 340a and 340b can comprise tissue (e.g., creped tissue, such as 17 gsm dry-creped tissue).

In dryness layer 332 of garment 300c-1, strips 336a and 336b are spaced laterally apart along a width of the dryness layer such that a longitudinally-extending channel 424 is defined between strip 336a and strip 336b. In some garments, each of the two strips has a lateral width that is equal to a lateral width of the other one of the two strips. In some garments, the lateral width of each of the two strips is between 15 and 30 mm, for example between 15 and 25 mm, between 17 and 23 mm (e.g., equal to 20 mm), and/or between 20 and 25 mm (e.g., equal to 22 mm). In some garments, the dryness layer and/or the nonwoven sheet has a width of between 50 and 100 mm, between 60 and 90 mm, and/or between 70 and 80 mm (e.g., equal to 75 mm). In some garments, the two strips of laminate are spaced apart by a lateral distance that is greater than a width of either of the two strips; for example, a lateral distance of between 25 and 50 mm, between 30 and 45 mm, between 30 and 40 mm (e.g., equal to 35 mm), and/or between 30 and 35 mm (e.g., 31 mm). For example, in garment 300c-1, the dryness layer has an overall width of 75 mm, strip 336a has a width of 20 mm, strip 336b has a width of 20 mm, and channel or distance 432 is equal to 35 mm.

FIGS. 3B, 3C, 4, 5B, and 6B are exaggerated to better understand the overall structure of the present garments (e.g., 300a-300c), laminates (e.g., 336), and dryness layers (e.g., 332) and, as such, are for illustrative purposes and are not necessarily to scale. For example, the figures illustrate the relative positions and relationships between elements of the present garments, including, for example, the position of laminae in a laminate (e.g., 336, 336a-336c), the general folded structure of a laminate (e.g., 336), and the manner by which dryness layer channel(s) (e.g., 368, 408a-408b, 424a-424b) can be defined, and should not be interpreted to limit the invention.

EXAMPLES

The present invention will be described in greater detail by way of specific examples. The follow examples are offered for illustrative purposes only and are not intended to limit the invention in any manner. Those of skill in the art will readily recognize a variety of noncritical parameters that can be changed or modified to yield essentially the same results.

Example 1

Three dryness layer models were produced. The first model ("Model 1") comprised a laminate having an absorbent lamina comprising 60 gsm HP500E SAP from Sumitomo Seika Chemicals Co., Ltd. in Osaka, Japan disposed between a first substrate lamina comprising 17 gsm 3995 tissue from Dunn Paper in East Hartford, Conn. and a second substrate lamina comprising a 50 gsm, 50% PET/50% VS spunlace nonwoven. Model 1's laminate was not folded.

The second model ("Model 2") comprised the same laminate as Model 1, but was folded as described in reference to garment 300a. The channel defined between the folded layers of Model 2 was 15 mm wide.

The third model ("Model 3") comprised a laminate having an absorbent lamina comprising 60 gsm HP500E SAP from Sumitomo Seika Chemicals Co., Ltd. in Osaka, Japan disposed between a first substrate lamina comprising 17 gsm dry-creped tissue from Dunn Paper in East Hartford, Conn. and a second substrate lamina comprising a 45 gsm resin-bonded polyester fiber nonwoven from Fitesa in Simpsonville, S.C. Model 3 was folded as described in reference to garment 300b. The channel defined between the folded layers of Model 3 was 15 mm wide and a middle laminate was disposed on the base layer within the channel.

Runoff performance of the models was compared. Each of the models was included in a diaper, with the dry layer placed on top of a conventional fluff/SAP core and a topsheet disposed on top of the laminate. The diaper incorporating Model 3 had light glue under the topsheet. In each of the Urine Runoff tests, three doses of 75 ml of liquid were metered to the diaper at a rate of approximately 800 ml/min. Runoff was collected and measured between each dose. Three samples of Model 1 and of Model 2 were tested and one sample of Model 3 was tested. The results are set forth in TABLE 1.

TABLE 1

RUNOFF TESTING OF SOME OF THE PRESENT DRYNESS LAYERS

| Model | Sample | Runoff - Dose 1 | Runoff - Dose 2 | Runoff - Dose 3 |
|---|---|---|---|---|
| 1 | 1 | 29.76 | 17.59 | 16.92 |
|   | 2 | 23.89 | 4.15 | 12.68 |
|   | 3 | 35.19 | 5.92 | 18.65 |
| 2 | 1 | 12.39 | 8.49 | 17.51 |
|   | 2 | 3.87 | 3.88 | 8.80 |
|   | 3 | 7.77 | 9.86 | 10.66 |
| 3 | 1 | 5.52 | 3.27 | 6.57 |

Model 2 exhibited less runoff compared to Model 1, indicating improved liquid acquisition. The improved liquid acquisition may be due to the folded laminate structure of Model 2, whose channel would facilitate liquid acquisition and distribution to the absorbent core and SAP in the laminate. Model 3 exhibited less runoff than Model 1 and Model 2. Model 3's superior liquid acquisition may be due to the different substrates used in the laminate and/or the multiple side channels defined between the middle laminate and the folded layers in Model 3.

Example 2

Three additional dryness layer models were produced and size large baby diaper samples were manufactured with respective dryness layer models disposed between the diaper samples' respective topsheets and absorbent cores. The fourth model ("Model 4") comprised a laminate having an absorbent lamina comprising 50 gsm SAP between a first substrate lamina comprising 17 gsm 3995 Tissue from Dunn Paper in East Hartford, Conn. and a second substrate lamina comprising an 11 gsm blue-colored spunbond nonwoven from Fitesa. Rather than being folded, Model 4 was arranged with two strips of the laminate as in garment 300c-1 but with the first substrate lamina adhered to a 75 mm wide strip of 70 gsm through-air-bonded (TAB) nonwoven. The two strips of the laminate were 22 mm wide, and were spaced apart by a lateral distance of 31 mm. The colored nonwoven is arranged to be visible through the topsheet when wet and, in other configurations, the second lamina could be adhered to the TAB nonwoven.

The fifth model ("Model 5") comprised a laminate having an absorbent lamina comprising 50 gsm SAP between a first substrate lamina comprising 17 gsm 3995 Tissue from Dunn Paper in East Hartford, Conn. and a second substrate lamina comprising an 11 gsm blue-colored spunbond nonwoven from Fitesa. Rather than being folded, Model 4 was arranged with three strips of the laminate as in garment 300c but with the first substrate lamina adhered to a 75 mm wide strip of 50 gsm through-air-bonded (TAB) nonwoven. The first strip of the laminate was 25 mm wide, and the second and third strips of the laminate were 12.5 mm wide arranged on opposite sides of the first strip, and were each spaced apart from the first strip by a lateral distance of 12.5 mm. The colored nonwoven is arranged to be visible through the topsheet when wet and, in other configurations, the second lamina could be adhered to the TAB nonwoven.

The sixth model ("Model 6") was similar to Model 5, with the exception that the TAB nonwoven had a basis weight of 70 gsm.

In the baby diaper samples, including a Bering control sample diaper, the absorbent cores were each manufactured with 10.8 grams of fluff and 9.0 grams of SAP, the overall diaper weight varied as indicated in Table 2, in which COV refers to coefficient of variation.

TABLE 2

DIAPER SAMPLE WEIGHT

| | Control | | Model 4 | | Model 5 | | Model 6 | |
|---|---|---|---|---|---|---|---|---|
| | Mean (grams) | COV (%) | Mean (grams) | COV (%) | Mean (grams) | COV (%) | Mean (grams) | COV (%) |
| Diaper Weight (n = 30) | 29.6 | 3.0 | 30.9 | 3.2 | 30.7 | 3.4 | 31.3 | 3.1 |

The Retention Under Load (RUL), Absorbency Against Pressure (AAP), Core Efficiency, Urine Run Off, Acquisition Time, Surface Conductivity, and Rewet were also measured.

As shown in Table 3, the Retention Under Load (RUL) for Models 4-6 was higher, and therefore better, than for the control. In Table 3, the mean values of RUL are listed in grams per square centimeter (g/cm$^2$) and were obtained under a pressure of 0.7 pounds per square inch (psi). Groupings were determined using the Tukey Method and 80% Confidence.

TABLE 3

RETENTION UNDER LOAD (g/cm$^2$)

| Model | No. of Samples | Mean | Grouping | | |
|---|---|---|---|---|---|
| 4 | 3 | 1.5291 | A | B | C |
| 5 | 3 | 1.6484 | A | B | |
| 6 | 3 | 1.6800 | A | | |
| Control | 3 | 1.4460 | A | B | C |

As shown in Table 4, the Absorbency Against Pressure (AAP) for Models 4-6 was higher, though perhaps not to a statistically significant degree, than for the control. In Table 4, the mean values of AAP are listed in grams per square centimeter (g/cm$^2$) and were obtained under a pressure of 0.7 pounds per square inch (psi). Groupings were determined using the Tukey Method and 80% Confidence.

TABLE 4

ABSORBENCY AGAINST PRESSURE (g/cm$^2$)

| Model | No. of Samples | Mean | Grouping | | |
|---|---|---|---|---|---|
| 4 | 3 | 1.1159 | A | B | |
| 5 | 3 | 1.0837 | A | B | C |
| 6 | 3 | 1.1577 | A | | |
| Control | 3 | 1.0027 | A | B | C |

As shown in Table 5, the Core Efficiency for Model 4 was higher, and therefore better, than for Models 5-6 and the control. In Table 5, the mean values of Core Efficiency correspond to AAP/RUL and are dimensionless (if multiplied by 100%, they could be reported in percent). Groupings were determined using the Tukey Method and 80% Confidence.

TABLE 5

CORE EFFICIENCY

| Model | No. of Samples | Mean | Grouping | | |
|---|---|---|---|---|---|
| 4 | 3 | 0.7300 | A | B | |
| 5 | 3 | 0.6572 | | | C |
| 6 | 3 | 0.6900 | | B | C |
| Control | 3 | 0.6944 | | B | C |

As shown in Tables 6-8, the Urine Run-Off for Models 5-6 was lower, and therefore better, than for the control. Tables 6-8 show measurements for doses 1-3, respectively, with each dose being 75 milliliters (mL) of 0.9% saline at a temperature of 40° C. delivered at a rate of 300 mL per minute (mL/min.), with 12 minutes between doses. In Tables 6-8, the mean values of Urine Run-Off are listed in grams (g). Groupings were determined using the Tukey Method and 80% Confidence.

TABLE 6

URINE RUN-OFF - DOSE 1

| Model | No. of Samples | Mean | Grouping |
|---|---|---|---|
| 4 | 3 | 0.127 | B |
| 5 | 3 | 0.393 | B |
| 6 | 3 | 0.127 | B |
| Control | 3 | 9.900 | A |

TABLE 7

URINE RUN-OFF - DOSE 2

| Model | No. of Samples | Mean | Grouping |
|---|---|---|---|
| 4 | 3 | 0.000 | B |
| 5 | 3 | 0.000 | B |
| 6 | 3 | 0.000 | B |
| Control | 3 | 4.610 | A |

TABLE 8

URINE RUN-OFF - DOSE 3

| Model | No. of Samples | Mean | Grouping |
|---|---|---|---|
| 4 | 3 | 0.000 | B |
| 5 | 3 | 0.000 | B |
| 6 | 3 | 0.000 | B |
| Control | 3 | 8.160 | A |

Liquid Acquisition is the time in seconds required to absorb a given volume of liquid.

REWET, the amount of liquid that can be expressed from an absorbent core under pressure, is a conventional measure of dryness for an absorbent product. In general, REWET increases abruptly once the absorbent capacity of the core is exceeded. REWET can be improved by increasing the absorbent capacity of the absorbent core and/or by isolating the diaper topsheet from the absorbent core with a high-loft nonwoven ADL. However, neither of these approaches reduces urine that can become trapped in the nonwoven topsheet of the product during the early stages of use.

Surface Conductivity is a measure of the dryness of the diaper samples—i.e., of the topsheet of the respective diaper. Surface Conductivity provides a measure of very small amounts of urine that can remain trapped in the topsheet of an absorbent product during use. When this moisture becomes isolated from (not directed toward the absorbent core), the moisture in the topsheet is eventually absorbed by the skin, and can reduce the natural barrier properties of the skin and make the skin more susceptible to any irritant that may be present. The present configurations of dryness layers can improve the dryness (reduce the surface conductivity) of an absorbent product by reducing the amount of urine trapped in the topsheet—while keeping the REWET of the product low. This is important because about 65% of baby diapers end up containing only 150 mL or less of urine. When a diaper contains less than 150 mL of urine, the urine trapped in the topsheet of the product that determines its dryness—i.e., under such circumstances the REWET, or amount of liquid that can be expressed from the core under pressure, does not determine product dryness. Surface Conductivity was measured over time—after delivery of a single, 130 ml dose of 0.9% saline at 40° C.—using an eight-pin conductivity Hydration Probe available from Cortex Technology in Hadsund, Denmark. The probe was weighted to provide a consistent load of 160-180 grams (g). for each measurement.

As shown in Table 9, Liquid Acquisition is shown in seconds (s), Surface Conductivity is shown in micro-Siemens (µS), and REWET is shown in grams (g).

TABLE 9

LIQUID ACQUISITION, SURFACE CONDUCTIVITY, REWET

| | | Control | | Model 4 | | Model 5 | | Model 6 | |
|---|---|---|---|---|---|---|---|---|---|
| | | Rep 1 | Rep 2 | Rep 1 | Rep 2 | Rep 1 | Rep 2 | Rep 1 | Rep 2 |
| Acquisition Time (s) | | 27 | 26 | 21 | 23 | 29 | 32 | 23 | 23 |
| Surface | t = 2' | 151 | 180 | 215 | 224 | 151 | 198 | 206 | 232 |
| Conductivity | t = 4' | 92 | 129 | 161 | 155 | 104 | 133 | 143 | 173 |
| (µS) | t = 8' | 71 | 84 | 144 | 131 | 78 | 108 | 141 | 135 |
| | t = 12' | 56 | 74 | 124 | 119 | 69 | 90 | 122 | 115 |
| | t = 16' | 43 | 65 | 106 | 114 | 67 | 81 | 117 | — |
| | t = 30' | 22 | 33 | 108 | 113 | 65 | 72 | 97 | 93 |
| REWET (g) | | 0.06 | 0.17 | 0.16 | 0.16 | 0.13 | 0.14 | 0.17 | 0.14 |

Test Methods

1. Urine Runoff Tests

To measure Urine Run-Off of a sample, a pump was calibrated to deliver the specified doses of 0.9% saline solution at the specified flow rate. A first end of pump tubing was connected to the pump and a second end of the pump tubing was connected to a metal nozzle having an aperture with a 0.094 inch internal diameter such that the pump could deliver a dose through the nozzle. The sample was placed on a plastic plate resting on a stand such that the plate was disposed at a 20-degree angle from the horizontal, with the sample's topsheet facing upward. The center of the dryness layer was marked and the tubing and metal nozzle were positioned such that the pump was configured to deliver doses to the marked center. A scale was tarred to the weight of a tray and the tray was positioned such that, after a dose was applied to the sample, any resulting runoff could fall from the plastic plate and collect in the tray.

Before dosing the sample, the saline solution was preheated to a temperature of 40° C. Each of the doses was applied by operating the pump to deliver the specified dose volume at the specified flow rate. For each of the doses, after the specified volume was reached, flow was stopped and any runoff was allowed to collect into the tray over a period of 5 minutes. After 5 minutes passed, the tray with any collected runoff was weighed and the amount of runoff for that dose was recorded as the change in tray weight. The tray was dried after being weighed and the process was repeated for subsequent doses.

2. RUL, AAP, and Core Efficiency

To measure the RUL, AAP, and Core Efficiency of a sample, a glass frit was soaked in a 0.9% saline solution. The soaked frit was placed into a dish, the dish was filled with additional saline solution until the saline level reached the top of the frit, and a 90 mm diameter filter paper was placed on the frit.

A cylinder assembly having an outer cylinder with a mesh filter on a lower end thereof and an inner plastic cylinder disposed in the outer cylinder was weighed. The sample was thereafter placed in the cylinder assembly at the lower end thereof such that pressure could be applied to the sample and the sample-containing assembly was weighed—that weight was recorded as "Sample Wt."

To measure AAP, a 1 kg cylinder weight was placed on the upper end of the cylinder assembly such that pressure was exerted on the sample and the lower end of the assembly was placed on the center of the frit such that the sample could absorb saline solution. The sample-containing cylinder assembly was allowed to remain on the frit for 30 minutes, after which the assembly was removed and any liquid droplets that accumulated underneath the mesh were wiped away. The cylinder assembly with the wet sample was weighed after removing the 1 kg cylinder weight—that weight was recorded as "AAP Wt." The sample's AAP was calculated by subtracting the Sample Wt. from the AAP Wt. and dividing the difference by the area of the sample.

To measure RUL, the cylinder assembly with the wet sample was placed back on the frit—without the 1 kg cylinder weight—such that the sample could continue to absorb saline solution. After 30 minutes, the 1 kg cylinder weight was placed on the cylinder assembly and, 30 minutes after doing so, the assembly was removed from the frit. The cylinder assembly with the wet sample (and without the 1 kg cylinder weight) was weighed—that weight was recorded as "RUL Wt." RUL was calculated by subtracting Sample Wt. from the RUL Wt. and dividing the difference by the area of the sample.

Core Efficiency was calculated by determining the sample's AAP and RUL in units of grams per gram (g/g) of SAP in the sample and, in terms of those units, dividing AAP by RUL. The following expressions were to determine AAP and RUL as expressed in g/g of SAP:

$$AAP_{(g/g)} = \frac{(AAP \text{ Wt.} - \text{Sample Wt.}) - (4.6 * W_T)}{W_{SAP}}$$

$$RUL_{(g/g)} = \frac{(RUL \text{ Wt.} - \text{Sample Wt.}) - (4.95 * W_T)}{W_{SAP}}$$

where $W_{SAP}$ and $W_T$ are the weights of SAP and tissue, respectively, in the sample.

3. Acquisition Time and Rewet

To determine acquisition time and rewet for a sample, the sample was secured on top of a foam pad—which was covered in a hydrophobic plastic—using tape. A 30.5 cm×15 cm×1.2 cm plastic block with a 5.4 cm diameter hole was placed on the sample such that the hole was oriented above the dryness layer of the sample at the center of the foam pad. A cylindrical dosing head was placed in the hole on top of the sample and a weight was placed on top of the dosing head. A timer was started and a first 75 mL dose was poured into the dosing head, and thus onto the sample, over 5 seconds. The timer was stopped once all the liquid was absorbed into the sample, which was recorded as the acquisition time.

To determine rewet, a second 75 ml dose was applied in this manner, a timer was set for 30 minutes, and at the end of the 30 minutes a third 75 ml dose was applied in the same manner as well. The timer was set for 30 minutes again and at the end of the 30 minutes a stopwatch was started and the plastic block was removed from the sample. When the stopwatch reached 30 seconds, a 3.5 g stack of filter paper and a 1.5 kg weight were placed on the center of the sample, the weight was removed after the stopwatch reached 2 minutes 25 seconds, and the wet mass of the stack of filter paper was measured. Rewet was calculated by subtracting the dry mass of the stack of filter paper from the wet mass thereof.

4. Surface Conductivity

To measure the surface conductivity of a sample, the sample was equilibrated in a lab at 22° C. and 50% relative humidity for 24 hours before testing. Elastics were removed from the sample and the sample was placed over a foam rubber pad with the ends of the sample secured to a bench top with tape such that the sample could lay flat over the pad. A polycarbonate plate with a hole was placed over the sample such that the hole was oriented over the dryness layer of the sample. A cylindrical dosing head was placed in the hole on top of the sample and a weight was placed on top of the dosing head. The sample was dosed with 130 mL of a 0.9% saline solution preheated to 40° C. at a rate of 20 mL/s. A timer was started and the dosing head was removed. Six surface conductivity measurements were taken over time: one at 2 minutes, one at 4 minutes, one at 8 minutes, one at 12 minutes, one at 16 minutes, and one at 30 minutes. For each, the measurement was taken by placing a surface conductivity probe on the surface of the product through the plate's hole at the "12 o'clock position" thereof such that the probe stood freely under its own weight, holding the probe for 3 seconds until a test value appeared, repositioning the probe and repeating that measurement at the 6 o'clock, 9 o'clock, and 3 o'clock positions, and averaging the measurements at each position to yield the surface conductivity at that point in time.

The above specification and examples provide a complete description of the structure and use of illustrative embodiments. Although certain embodiments have been described above with a certain degree of particularity, or with reference to one or more individual embodiments, those skilled in the art could make numerous alterations to the disclosed embodiments without departing from the scope of this invention. As such, the various illustrative embodiments of the methods and systems are not intended to be limited to the particular forms disclosed. Rather, they include all modifications and alternatives falling within the scope of the claims, and embodiments other than the one shown may include some or all of the features of the depicted embodiment. For example, elements may be omitted or combined as a unitary structure, and/or connections may be substituted. Further, where appropriate, aspects of any of the examples described above may be combined with aspects of any of the other examples described to form further examples having comparable or different properties and/or functions, and addressing the same or different problems. Similarly, it will be understood that the benefits and advantages described above may relate to one embodiment or may relate to several embodiments.

The claims are not intended to include, and should not be interpreted to include, means-plus- or step-plus-function limitations, unless such a limitation is explicitly recited in a given claim using the phrase(s) "means for" or "step for," respectively.

The invention claimed is:

1. An absorbent garment comprising:
   a chassis having opposing front and rear waist portions, a crotch portion extending longitudinally between the front and rear waist portions, a topsheet, and a backsheet;
   an absorbent core coupled to the crotch portion; and
   a dryness layer extending longitudinally along the absorbent core and comprising:
      a nonwoven sheet; and
      two or more longitudinally-extending laminate strips coupled to the nonwoven sheet, each including an absorbent lamina, a first substrate lamina, and a second substrate lamina, the absorbent lamina disposed between the first and second substrate laminae, the absorbent lamina comprising superabsorbent polymer (SAP) and the first and second substrate laminae each comprising tissue or nonwoven;
   wherein the absorbent lamina, first substrate lamina, and second substrate lamina of each of the strips are separate from the absorbent lamina, first substrate lamina, and second substrate lamina of each other of the strips;
   wherein the strips are spaced apart laterally along a width of the dryness layer such that a longitudinally-extending channel is defined between a first one of the strips and a second one of the strips;
   wherein the absorbent core and the dryness layer are disposed between the topsheet and the backsheet.

2. The absorbent garment of claim 1, wherein the two or more strips includes first and second strips of equal lateral widths.

3. The absorbent garment of claim 2, wherein the channel has a lateral width that equal to or greater than a width of each of the first and second strips.

4. The absorbent garment of claim 2, wherein a lateral width of the channel is between 10 and 40 millimeters (mm).

5. The absorbent garment of claim 2, wherein a lateral width of each of the first and second strips is between 12 and 24 millimeters (mm).

6. The absorbent garment of claim 1, wherein the two or more strips includes a third strip with a lateral width that is at least 10% larger than the width of each of the first and second strips.

7. The absorbent garment of claim 6, wherein a lateral width of the third strip is between 20 and 30 millimeters (mm).

8. The absorbent garment of claim 1, wherein the width of the dryness layer is between 65 and 85 millimeters (mm).

9. The absorbent garment of claim 8, wherein the dryness layer has a longitudinal length between 185 and 270 millimeters (mm).

10. The absorbent garment of claim 1, wherein:
    the absorbent core has a lateral width at least 10% larger than the width of the dryness layer; and/or
    the absorbent core and the dryness layer each have a longitudinal length, the length of the absorbent core at least 10% larger than the length of the dryness layer.

11. The absorbent garment of claim 1, wherein for each of the strips the SAP of the absorbent lamina has a basis weight between 40 and 220 grams per square meter (gsm).

12. The absorbent garment of claim 1, wherein for each of the strips the tissue or nonwoven of each of the first and second substrate laminae has a basis weight between 10 and 20 gsm and, optionally, the tissue is creped.

13. The absorbent garment of claim 1, wherein the nonwoven sheet has a basis weight between 40 and 80 grams per square meter (gsm).

14. The absorbent garment of claim 1, wherein the nonwoven sheet comprises a through-air bonded polymer nonwoven.

15. The absorbent garment of claim 1, wherein the strips are disposed between the absorbent core and the nonwoven sheet such that the nonwoven sheet is disposed closer to a wearer than are the strips when the garment is worn.

* * * * *